United States Patent
Nishino et al.

(10) Patent No.: US 8,970,755 B2
(45) Date of Patent: Mar. 3, 2015

(54) RADIOGRAPHIC IMAGING DEVICE, RADIOGRAPHIC IMAGING SYSTEM, CONTROL METHOD, AND NON-TRANSITORY COMPUTER READABLE MEDIUM

(71) Applicant: FUJIFILM Corporation, Tokyo (JP)

(72) Inventors: Naoyuki Nishino, Kanagawa (JP); Naoto Iwakiri, Kanagawa (JP); Kouichi Kitano, Kanagawa (JP); Yasunori Ohta, Kanagawa (JP); Haruyasu Nakatsugawa, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 14/478,833

(22) Filed: Sep. 5, 2014

(65) Prior Publication Data
US 2014/0374610 A1    Dec. 25, 2014

Related U.S. Application Data

(63) Continuation of application No. PCT/JP2013/055525, filed on Feb. 28, 2013.

(30) Foreign Application Priority Data

Mar. 9, 2012  (JP) .................................. 2012-053853
Mar. 9, 2012  (JP) .................................. 2012-053854

(51) Int. Cl.
*H01L 27/146*   (2006.01)
*G01T 1/20*     (2006.01)
(Continued)

(52) U.S. Cl.
CPC ............ *H01L 27/14612* (2013.01); *G01T 1/24* (2013.01)

USPC ................ 348/297; 250/370.09; 250/370.11; 348/308

(58) Field of Classification Search
CPC . H04N 3/155; H04N 5/35554; H04N 5/3535; H04N 5/353
USPC ................ 250/370.09, 370.11; 348/297, 308
See application file for complete search history.

(56) References Cited

U.S. PATENT DOCUMENTS

2003/0215058 A1    11/2003  Kinno et al.
2009/0001276 A1*    1/2009  Yagi et al. ................ 250/370.09
2012/0086840 A1*    4/2012  Xhakoni et al. ............. 348/297

FOREIGN PATENT DOCUMENTS

JP          3696176 B2     9/2005
JP       2010-268171 A    11/2010

OTHER PUBLICATIONS

AGC (Asahi Glass Co., Ltd.). "Successful Development of World's Thinnest Ultra-thin Plate Glass (0.1 mm) by a Float Process", May 16, 2011, Internet <URL: http://www.agc.com/news/2011/0516.pdf>.

(Continued)

*Primary Examiner* — David J Makiya
*Assistant Examiner* — Kenneth J Malkowski
(74) *Attorney, Agent, or Firm* — Birch, Stewart, Kolasch & Birch, LLP

(57) ABSTRACT

The present invention may suppress feedthrough components in video imaging. Namely, TFT driving waveforms are plurally overlapped, and an integration period of capacitors C of amplification circuits is set so as to encompass a generation period of a feedthrough component (OFF), a generation period of a feedthrough component (ON), and a period in which charges (a signal component) are read out from storage capacitors of pixels by ON states of the TFTs. A number of driving waveforms to be overlapped is determined in accordance with a frame rate, the integration period and a reset period, or the like.

15 Claims, 27 Drawing Sheets

(51) Int. Cl.
*H04N 3/14* (2006.01)
*G01T 1/24* (2006.01)

(56) References Cited
OTHER PUBLICATIONS

International Search Report issued in PCT/JP2013/055525, mailed on Apr. 2, 2013.
PCT/ISA/237 issued in PCT/JP2013/055525, mailed on Apr. 2, 2013.

* cited by examiner

RADIOGRAPHIC IMAGING DEVICE, RADIOGRAPHIC IMAGING SYSTEM, CONTROL METHOD, AND NON-TRANSITORY COMPUTER READABLE MEDIUM

CROSS-REFERENCE TO RELATED APPLICATIONS

This application is a continuation application of International Application No. PCT/JP2013/055525, filed Feb. 28, 2013, the disclosure of which is incorporated herein by reference in its entirety. Further, this application claims priority from Japanese Patent Application No. 2012-053853, filed Mar. 9, 2012, and Japanese Patent Application No. 2012-053854, filed Mar. 9, 2012, the disclosures of which are incorporated herein by reference in their entirety.

BACKGROUND OF THE INVENTION

1. Field of the Invention

The present invention relates to a radiation imaging device, a radiation imaging system, a radiation imaging device control method, and a non-transitory computer readable medium storing a radiation imaging device control program. In particular, the present invention relates to a radiation imaging device, a radiation imaging system, a radiation imaging device control method, and a non-transitory computer readable medium storing radiation imaging device control program that may image still images and video images.

2. Description of the Related Art

Heretofore, a radiation imaging device has been known that, in order to image a radiation image, detects radiation that has been irradiated from a radiation irradiation device and has passed through an imaging subject, with a radiation detector. This radiation imaging device performs imaging of radiation images that are still images and also, for example, imaging of video images in which plural radiation images (still images) are successively imaged.

This radiation imaging device includes the radiation detector that detects radiation. The radiation detector is a detector that includes pixels and amplification circuits or the like; each pixel includes a photoelectric conversion element, a storage capacitor and a switching element. The photoelectric conversion element generates charges due to irradiation of radiation or illumination of light converted from radiation. The storage capacitor retains and accumulates the charges generated by the photoelectric conversion element. The switching element reads the charges out from the storage capacitor and outputs electronic signals that correspond to the charges. Each amplification circuit is configured by an integration circuit, which integrates charges that correspond to the electronic signals outputted from a switching element provided at a pixel, and outputs electronic signals for which the integrated charges are amplified.

In a case in which a large number of switching elements such as TFTs or the like are arranged in a matrix pattern, plural gate lines for turning the switching elements ON and OFF, and plural signal lines for transferring the signal charges from pixels whose switching elements have been turned ON, form an intersecting arrangement, and thus, parasitic capacitances occur. The amplitude of a voltage applied to a parasitic capacitance occurring at intersecting position of the gate line and signal line connected to a switching element changes in a case in which the switching element is turned ON or turned OFF. Thus, induced charges are produced at the parasitic capacitance, and these charges are superimposed on the charges being transferred through the signal line (signal charges for a radiation image) in the form of a noise component which is referred to as a "feedthrough component". Since the charge amounts retained and accumulated at the individual pixels of the radiation detector are very small, the signal charges being transferred along the signal lines are of the same order as the order of the feedthrough components. Therefore, the effects of the feedthrough components cannot be disregarded.

Accordingly, as technologies for eliminating (cancelling) the feedthrough components, for example. Japanese Patent No. 3,696,176 and Japanese Patent Application Laid-Open (JP-A) No. 2010-268171, discloses such the technologies.

In general, in imaging a video image, plural frames (a plural number) of still images are successively imaged. In cases of imaging these video images, it is desirable to increase the frame rate. In particular, higher frame rates have been called for in recent years.

However, the effects of the above-described feedthrough components may become larger in a case of video imaging. In video imaging, because plural images (frames) are being imaged, doses for each frame are smaller than in a case in which imaging still images. Consequently, the charge amounts retained and accumulated at the pixels become smaller, and the effects of the feedthrough components become relatively larger.

The present invention provides a radiation imaging device, radiation imaging system, radiation imaging device control method, and non-transitory computer readable medium storing radiation imaging device control program that may suppress feedthrough components in imaging video images.

SUMMARY OF THE INVENTION

A first aspect of the present invention is a radiation imaging device including: a radiation detector including plural scan lines disposed in parallel, and plural pixels disposed in a matrix pattern, each pixel including a sensor portion that generates charges in response to irradiated radiation and a switching element that is controlled to ON state or OFF state in accordance with a state of a control signal flowing along a particular scan line, wherein switching elements read out the charges generated by the sensor portions; plural amplifier sections, disposed in correspondence with the pixels of the radiation detector, each amplifier section being provided with an integrating capacitor that integrates the charges and a reset section that resets charges in the integrating capacitor, the plural amplifier sections amplifying electronic signals based on the charges read out from the corresponding pixels by the switching elements by a predetermined amplification ratio; a setting section that sets an integration period of the integrating capacitors, the integration period encompassing a first integration period for integrating a feedthrough component generated by a first of the switching elements of a first of the pixels being put into the OFF state by a control signal flowing through a particular scan line, and a second integration period for integrating a feedthrough component generated by a second of the switching elements of a second of the pixels, in which a timing for reading out the charges are plural cycles later than the first pixel based on a frame rate, being put into the ON state and the charges read out from the second pixel due to this ON state; and a control section is configured to put the first switching element into the OFF state and to put the second switching element into the ON state within the integration period set by the setting section.

A second aspect of the present invention, in the above first aspect, further includes a temperature detection section that detects a temperature of the radiation detector, wherein a correspondence between temperature and time constants of the feedthrough components is determined in advance, and wherein, on the basis of a temperature detected by the temperature detection section, the control section puts the first switching element into the OFF state and puts the second switching element into the ON state at timings in accordance with the time constants of the feedthrough components.

A third aspect of the present invention, in the above second aspect, the control section puts the first switching element into the OFF state and puts the second switching element into the ON state at timings in accordance with the time constants of the feedthrough components, on the basis of temperatures detected by the temperature detection section at a timing of at least one of a start of imaging or a cycle of a predetermined number of frames.

A fourth aspect of the present invention, in the above second aspect, the temperature detection section detects the temperature of at least one predetermined region of a region of the radiation detector on which the radiation is irradiated, and the control section puts the first switching element into the OFF state and puts the second switching element into the ON state at timings in accordance with the time constants of the feedthrough components on the basis of the temperature of the predetermined region detected by the temperature detection section.

A fifth aspect of the present invention, in any of the above first to fourth aspects, amplitudes of the feedthrough components are determined in advance for each of predetermined regions of a region of the radiation detector on which the radiation is irradiated, and the control section puts the first switching element into the OFF state and puts the second switching element into the ON state at timings in accordance with the predetermined amplitudes and the time constants of the feedthrough components for each predetermined regions.

A sixth aspect of the present invention, in the above fifth aspect, further includes a receiving section that receives a designation of the predetermined regions, wherein the control section puts the first switching element into the OFF state and puts the second switching element into the ON state at timings in accordance with the predetermined amplitudes and the time constants of the feedthrough components for the predetermined region received by the receiving section.

A seventh aspect of the present invention, in any of the above first to sixth aspects, the setting section sets the timing for reading out the charges from the second pixel to be plural cycles later than the first pixel, in accordance with a type of video image being imaged with the radiation detector.

An eighth aspect of the present invention, in any of the above first to seventh aspects, in a case in which a video image is being imaged with the radiation detector, the control section acquires a frame rate of the video imaging and, in a case in which the frame rate is equal to or higher than a predetermined threshold, puts the first switching element into the OFF state and puts the second switching element into the ON state at timings in accordance with the time constants of the feedthrough components.

A ninth aspect of the present invention, in any of the above first to eighth aspects, in a case in which a dose of the radiation irradiated at the radiation detector is equal to or lower than a predetermined threshold, the control section puts the first switching element into the OFF state and puts the second switching element into the ON state at timings in accordance with the time constants of the feedthrough components.

A tenth aspect of the present invention, in any of the above first to ninth aspects, depending on a type of video imaging, the control section puts the first switching element into the OFF state and puts the second switching element into the ON state at timings in accordance with the time constants of the feedthrough components.

An eleventh aspect of the present invention, in any of the above first to tenth aspects, in a case in which a video image is imaged with the radiation detector, the control section acquires a frame rate of the video imaging and, in a case in which the acquired frame rate is equal to or higher than a predetermined threshold, the control section puts the first switching element into the OFF state and puts the second switching element into the ON state at timings such that a period in which the first switching element is in the ON state and a period in which the second switching element is in the ON state overlap, and such that an overlap period of this overlapping is shorter than an overlap period in a case in which the frame rate is lower than the predetermined threshold.

A twelfth aspect of the present invention, in any of the above first to eleventh aspects, the setting section sets to cause the first integration period and the second integration period to overlap.

A thirteenth aspect of the present invention is a radiation irradiation device; and a radiation imaging device according to claim 1 that detects radiation irradiated from the radiation irradiation device.

A fourteenth aspect of the present invention is a control method of a radiation imaging device including plural scan lines disposed in parallel, and plural pixels disposed in a matrix pattern, each pixel including a sensor portion that generates charges in response to irradiated radiation and a switching element that is controlled to ON state or OFF state in accordance with a state of a control signal flowing along a particular scan line, wherein the switching element read out the charges generated by the sensor portions, and plural amplifier sections, disposed in correspondence with the pixels of the radiation detector, each amplifier section being provided with an integrating capacitor that integrates the charges and a reset section that resets charges in the integrating capacitor, the plural amplifier sections amplifying electronic signals based on the charges read out from the corresponding pixels by the switching elements by a predetermined amplification ratio, the control method including: setting, by the setting section, an integration period of the integrating capacitors, the integration period encompassing, a first integration period for integrating a feedthrough component generated by a first of the switching elements of a first of the pixels being put into the OFF state by a control signal flowing through a particular scan line, and a second integration period for integrating a feedthrough component generated by a second of the switching elements of a second of the pixels, in which a timing for reading out the charges are plural cycles later than the first pixel based on a frame rate, being put into the ON state and the charges read out from the second pixel due to this ON state; and controlling, by a control section, to put the first switching element into the OFF state and to put the second switching element into the ON state within the integration period set by the setting section.

A fifteenth aspect of the present invention is a non-transitory computer readable medium storing a control program for a radiation imaging device, the radiation imaging device including plural scan lines disposed in parallel, and plural pixels disposed in a matrix pattern, each pixel including a sensor portion that generates charges in response to irradiated radiation and a switching element that is controlled to ON state or OFF state in accordance with a state of a control signal flowing along a particular scan line, wherein the switching element read out the charges generated by the sensor portions, and plural amplifier sections, disposed in correspondence with the pixels of the radiation detector, each amplifier section being provided with an integrating capacitor that integrates the charges and a reset section that resets charges in the integrating capacitor, and the plural amplifier sections amplifying electronic signals based on the charges read out from the corresponding pixels by the switching elements by a predetermined amplification ratio, the control program being executable to cause a computer to function as: a setting section that sets an integration period of the integrating capacitors, the integration period encompassing a first integration period for integrating a feedthrough component generated by a first of the switching elements of a first of the pixels being put into the OFF state by a control signal flowing through a particular scan line, and a second integration period for integrating a feedthrough component generated by a second of the switching elements of a second of the pixels, in which a timing for reading out the charges are plural cycles later than the first pixel based on a frame rate, being put into the ON state and the charges read out from the second pixel due to this ON state; and a control section that controls to put the first switching element into the OFF state and to put the second switching element into the ON state within the integration period set by the setting section.

According to the above aspects of the present invention, feedthrough components in imaging of a video image may be suppressed. Further, a frame rate in imaging of a video image may be raised.

BRIEF DESCRIPTION OF DRAWINGS

Detailed explanation follows regarding exemplary embodiments of the present invention, with reference to the following drawings.

DETAILED DESCRIPTION OF THE INVENTION

Herebelow, an example of a present exemplary embodiment is described with reference to the attached drawings.

First Exemplary Embodiment

Figure 1:
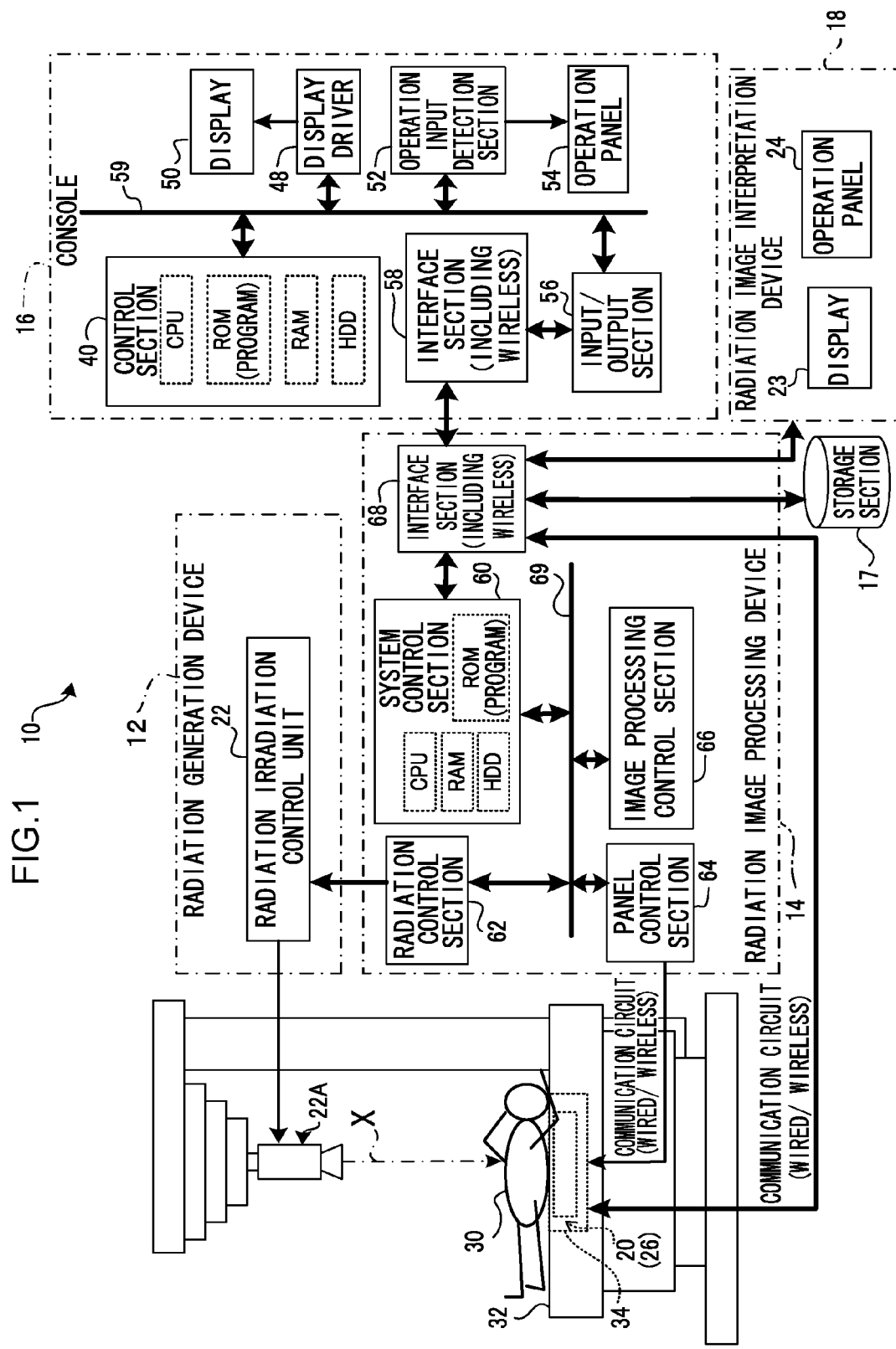
FIG. 1 is a schematic configurational diagram showing an outline of overall configuration of an example of a radiation imaging system in accordance with a first exemplary embodiment.

First, the overall schematic configuration of a radiation imaging system including a radiation image processing device according to the present exemplary embodiment is described. FIG. 1 shows a schematic configurational diagram of the schematics of the overall configuration of an example of the radiation image capture system according to the present exemplary embodiment. A radiation imaging system 10 according to the present exemplary embodiment may image both video images and still images. In the present exemplary embodiment, where not particularly specified, the term "radiation image" refers to both video images and still images. The meaning of the term "video image" as used in the present exemplary embodiment includes successive still images being rapidly displayed so as to be interpreted as moving images, in which a process of capturing a still image, converting it to electronic signals, transferring the electronic signals, and replaying the still image from the electronic signals is rapidly repeated. Thus, depending on the degree of "rapidity", imaging of (a portion or the whole of) the same region a plural number of times in a predetermined duration and successively replaying the images, which is known as "frame advance", is also encompassed by the term "video image".

The radiation image capture system 10 according to the present exemplary embodiment includes functions for capturing radiation images in response to operations by doctors, radiographers, and the like, ON the basis of instructions (imaging menu selections) inputted from an external system (for example, a radiology information system (RIS)) via a console 16.

The radiation image capture system 10 according to the present exemplary embodiment also includes functions that enable doctors, radiographers, and the like, to interpret radiation images, by displaying captured radiation images at a display 50 of the console 16 or at a radiation image interpretation device 18 or the like.

The radiation image capture system 10 according to the present exemplary embodiment includes a radiation generation device 12, a radiation image processing device 14, the console 16, a storage section 17, the radiation image interpretation device 18, and an electronic cassette 20.

The radiation generation device 12 includes a radiation irradiation control unit 22. The radiation irradiation control unit 22 has a function for causing an irradiation of radiation X from a radiation irradiation source 22A, at an imaging target region of an imaging subject 30 on an imaging table 32, in accordance with control by a radiation control section 62 of the radiation image processing device 14.

Radiation X that passes through the imaging subject 30 is irradiated onto the electronic cassette 20, which is retained at a retention portion 34 inside the imaging table 32. The electronic cassette 20 includes functions for generating electric charges in accordance with doses of the radiation X passing through the imaging subject 30, generating image information representing a radiation image based on the generated charge amounts, and outputting the image information. The electronic cassette 20 according to the present exemplary embodiment includes a radiation detector 26.

In the present exemplary embodiment, the image information representing a radiation image that is outputted by the electronic cassette 20 is inputted to the console 16 via the radiation image processing device 14. The console 16 according to the present exemplary embodiment includes functions for controlling the radiation generation device 12 and the electronic cassette 20, using imaging menu selections and various other kinds of information acquired from the external system (the RIS) or the like via a wireless network (a local area network (LAN)) or the like. The console 16 according to the present exemplary embodiment also includes functions for exchanging various kinds of information such as image information of radiation images with the radiation image processing device 14, and includes functions for exchanging various kinds of information with the electronic cassette 20.

The console 16 according to the present exemplary embodiment is a server computer. The console 16 includes a control section 40, a display driver 48, the display 50, an operation input detection section 52, an operation panel 54, an input/output section 56 and an interface section 58.

The control section 40 includes functions for controlling overall operations of the console 16, and is provided with a central processing unit (CPU), ROM, RAM and a hard disk drive (HDD). The CPU includes functions for controlling overall operations of the console 16. Various programs including a control program to be used at the CPU and suchlike are pre-memorized in the ROM. The RAM includes functions for temporarily storing various kinds of data. The HDD includes functions for storing and retaining various kinds of data.

The display driver 48 includes functions for controlling the display of various kinds of information at the display 50. The display 50 according to the present exemplary embodiment includes functions for displaying imaging menu items, captured radiation images and the like. The operation input detection section 52 includes functions for detecting operation states of the operation panel 54. The operation panel 54 is for doctors, radiographers and the like to input operation instructions in relation to the imaging of radiation images. The operation panel 54 according to the present exemplary embodiment includes, for example, a touch panel, a touch pen, plural buttons and a mouse, or the like. In a case in which the operation panel 54 is a touch panel, it may be the same component as the display 50.

The input/output section 56 and the interface section 58 exchange various kinds of information with the radiation image processing device 14 and the radiation generation device 12 by wireless communications, and include functions for exchanging various kinds of information such as image information with the electronic cassette 20.

The control section 40, the display driver 48, the operation input detection section 52 and the input/output section 56 are connected to transfer information and the like to one another by a bus 59, which is a system bus, a control bus or the like. Therefore, the control section 40 may control displays of various kinds of information at the display 50 via the display driver 48, and may control exchanges of various kinds of information with the radiation generation device 12 and the electronic cassette 20 via the interface section 58.

The radiation image processing device 14 according to the present exemplary embodiment includes functions for controlling the radiation generation device 12 and the electronic cassette 20 in accordance with instructions from the console 16. The radiation image processing device 14 also includes functions for memorizing radiation images received from the electronic cassette 20 in the storage section 17 and for controlling displays at the display 50 of the console 16 and the radiation image interpretation device 18.

The radiation image processing device 14 according to the present exemplary embodiment includes a system control section 60, the radiation control section 62, a panel control section 64, an image processing control section 66 and an interface section 68.

The system control section 60 includes functions for overall control of the radiation image processing device 14 and functions for controlling the radiation image capture system 10. The system control section 60 includes a CPU, ROM, RAM and an HDD. The CPU includes functions for controlling overall operations of the radiation image processing device 14 and operations of the radiation imaging system 10. Various programs including a control program to be used at the CPU and suchlike are pre-memorized in the ROM. The RAM includes functions for temporarily storing various kinds of data. The HDD includes functions for storing and retaining various kinds of data. The radiation control section 62 includes functions for controlling the radiation irradiation control unit 22 of the radiation generation device 12 in accordance with instructions from the console 16. The panel control section 64 includes functions for receiving information from the electronic cassette 20 by wireless and by wire. The image processing control section 66 includes functions for applying various kinds of image processing to radiation images.

The system control section 60, the radiation control section 62, the panel control section 64 and the image processing control section 66 are connected to be capable of transferring information and the like to one another by a bus 69, which is a system bus, a control bus or the like.

The storage section 17 according to the present exemplary embodiment includes functions for memorizing imaged radiation images and information relating to the radiation images. The storage section 17 may be, for example, an HDD or the like.

The radiation image interpretation device 18 according to the present exemplary embodiment is a device that includes functions for interpretation of the captured radiation images by radiographic interpretation staff. The radiation image interpretation device 18 is not particularly limited but may be a "radiographic interpretation viewer", a console, a tablet terminal or the like. The radiation image interpretation device 18 according to the present exemplary embodiment is a personal computer. The radiation image interpretation device 18, similarly to the console 16 and the radiation image processing device 14, is provided with a CPU, ROM, RAM, an HDD, a display driver, a display 23, an operation input detection section, an operation panel 24, an input/output section, and an interface section. Note that, in FIG. 1, to avoid complexity in the drawing, only the display 23 and the operation panel 24 are shown of these configurations, and the other configurations are not shown.

Now, the electronic cassette 20 is described in detail. First, the radiation detector 26 provided in the electronic cassette 20 is described. The radiation detector 26 according to the present exemplary embodiment includes a TFT substrate.

Figure 2:
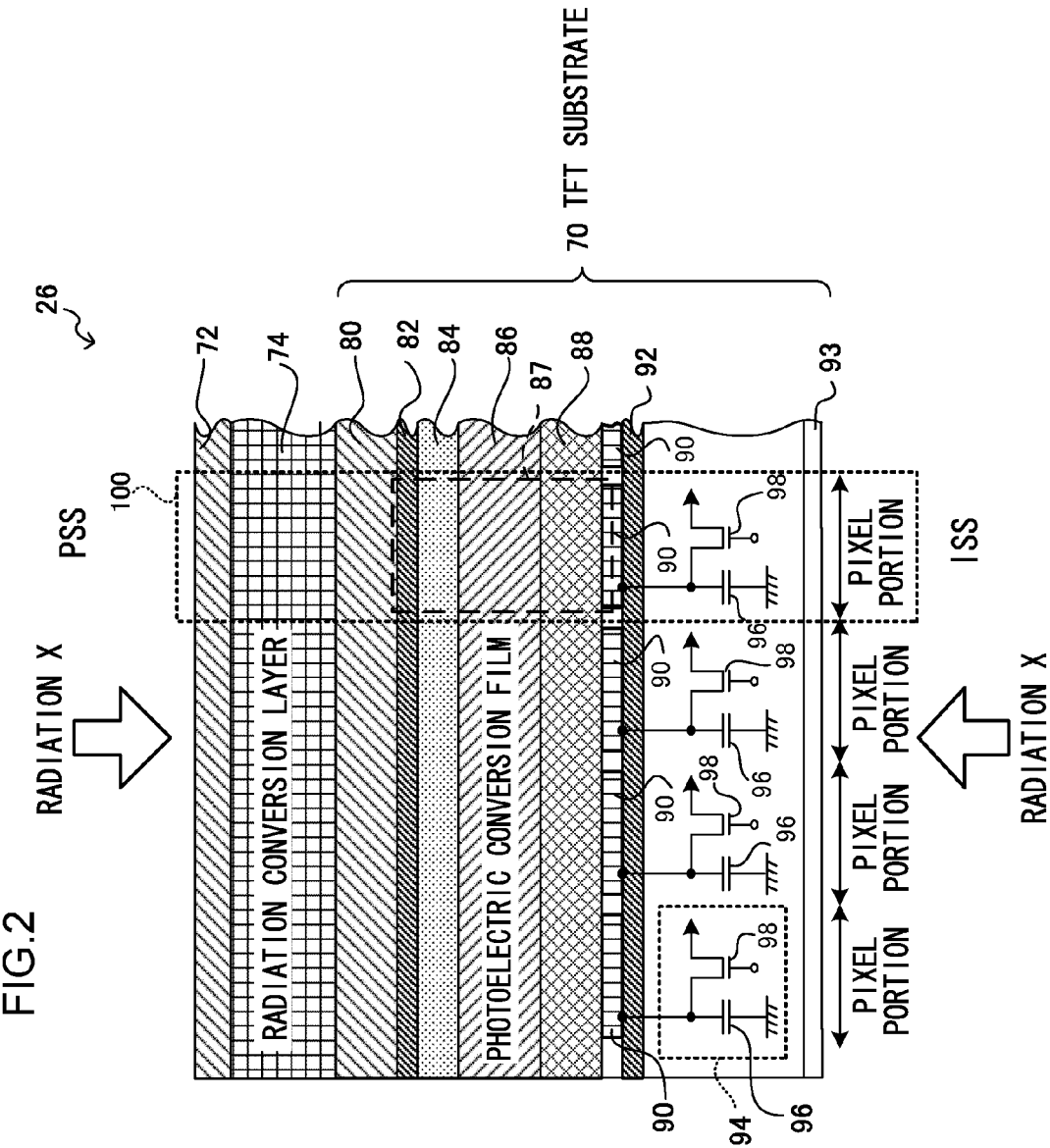
FIG. 2 is a schematic diagram showing an outline of a cross section of an example of an indirect conversion-type radiation detector in accordance with the first exemplary embodiment.

A schematic view of a cross section of an indirect conversion-type example of the radiation detector 26 is shown in FIG. 2 as an example of the radiation detector 26. The radiation detector 26 shown in FIG. 2 is provided with the TFT substrate and a radiation conversion layer.

A bias electrode 72 has a function of applying a bias voltage to a radiation conversion layer 74. In the present exemplary embodiment, the radiation detector 26 is a hole-reading sensor. Therefore, a positive bias voltage is provided to the bias electrode 72 from a high-voltage power supply, which is not shown in the drawings. In a case in which the radiation detector 26 is an electron-reading sensor that reads electrons generated in accordance with irradiated radiation X, a negative bias voltage is provided to the bias electrode 72.

The radiation conversion layer 74 is a scintillator. In the radiation detector 26 according to the present exemplary embodiment, the radiation conversion layer 74 is formed to be layered on a transparent insulating film 80 between the bias electrode 72 and an upper electrode 82. The radiation conversion layer 74 is formed as a film of a fluorescent material that converts radiation X that is incident from above or below to light and emits the light. Because this radiation conversion layer 74 is provided, the radiation X is absorbed and light is emitted.

The wavelength range of the light emitted by the radiation conversion layer 74 is preferably in the visible light range (wavelengths from 360 nm to 830 nm). To enable monochrome imaging by the radiation detector 26, it is more preferable if a green wavelength range is included.

As the scintillator that is used as the radiation conversion layer 74, a scintillator is desirable that produces fluorescent light with a relatively wide wavelength range, such that light in a wavelength range that can be absorbed at a TFT substrate 70 is produced. This kind of scintillator may include CsI:Na, $CaWO_4$, $YTaO_4$:Nb, BaFX:Eu (in which X is Br or Cl), LaOBr:Tm, GOS or the like. Specifically, in a case in which X-rays are used as the radiation X and imaged, it is preferable to include cesium iodide (CsI). It is particularly preferable to use cesium iodide with thallium added thereto (CsI:Tl), CsI: Na or the like, which have a light emission spectrum with a wavelength range of 400 nm to 700 nm in a case in which X-rays are irradiated thereon. CsI:Tl has a light emission peak wavelength of 565 nm, in the visible light region. If a scintillator containing CsI is to be used as the radiation conversion layer 74, it is preferable to use a scintillator that is formed with a strip-shaped columnar crystal configuration by vacuum vapor deposition.

Light produced by the radiation conversion layer 74 must be incident on a photoelectric conversion film 86. Therefore, an upper electrode 82 is preferably constituted with a conductive material that is transparent at least to a wavelength of light emitted from the radiation conversion layer 74. Specifically, it is preferable to use transparent conducting oxides (TCO) which have high transparency to visible light and low resistance values. A thin metal film of gold or the like may be used as the upper electrode 82. However, if the transparency is to be 90% or above, the resistance value is likely to be high. Therefore, a TCO is more preferable. For example, ITO, IZO, AZO, FTO, $SnO_2$, $TiO_2$, $ZnO_2$ or the like may be preferably used. In regard to ease of processing, low resistance and transparency, ITO is the most preferable. Herein, the upper electrode 82 may be formed as a single common electrode for all pixels, or may be divided for each the individual pixels.

The photoelectric conversion film 86 includes an organic photoelectric conversion material that absorbs the light emitted by the radiation conversion layer 74 and generates charges. The photoelectric conversion film 86 includes an organic photoelectric conversion material, absorbs light emitted from the radiation conversion layer 74, and generates electric charges in accordance with the absorbed light. If the photoelectric conversion film 86 includes this organic photoelectric conversion material, the film has a sharp absorption spectrum in the visible range. Therefore, hardly any electromagnetic waves apart from the light emitted by the radiation conversion layer 74 are absorbed by the photoelectric conversion film 86. Thus, noise that is caused by radiation X such as X-rays or the like being absorbed at the photoelectric conversion film 86 may be effectively suppressed.

For the organic photoelectric conversion material of the photoelectric conversion film 86 to absorb the light emitted by the radiation conversion layer 74 most efficiently, it is preferable that the absorption peak wavelength of the organic photoelectric conversion material be as close as possible to the light emission peak wavelength of the radiation conversion layer 74. It is ideal if the absorption peak wavelength of the organic photoelectric conversion material and the light emission peak wavelength of the radiation conversion layer 74 match. However, provided a difference between the two is small, the light emitted from the radiation conversion layer 74 can be satisfactorily absorbed. In specific terms, it is preferable if a difference between the absorption peak wavelength of the organic photoelectric conversion material and the light emission peak wavelength of the radiation conversion layer 74 in response to the radiation X is not more than 10 nm, and it is more preferable if the same is not more than 5 nm. Organic photoelectric conversion materials that may satisfy these conditions include, for example, quinacridone-based organic compounds and phthalocyanine-based organic compounds. For example, an absorption peak wavelength of quinacridone in the visible region is 560 nm. Therefore, if quinacridone is used as the organic photoelectric conversion material and CsI:Tl is used as the material of the radiation conversion layer 74, the difference between the peak wavelengths may be kept to within 5 nm. Hence, charge amounts generated in the photoelectric conversion film 86 may be substantially maximized.

To suppress an increase in dark current, it is preferable to provide one or other of an electron blocking film 88 and a hole blocking film 84, and it is more preferable to provide both. The electron blocking film 88 may be provided between a lower electrode 90 and the photoelectric conversion film 86. The electron blocking film 88 may suppress an increase in the dark current caused by electrons injected from the lower electrode 90 to the photoelectric conversion film 86, in a case in which a bias voltage is applied between the lower electrode 90 and the upper electrode 82. An organic material with electron affinity may be used for the electron blocking film 88. The hole blocking film 84 may be provided between the photoelectric conversion film 86 and the upper electrode 82. The hole blocking film 84 may suppress an increase in the dark current caused by holes injected from the upper electrode 82 to the photoelectric conversion film 86, in a case in which a bias voltage is applied between the lower electrode 90 and the upper electrode 82. An organic material with electron acceptance may be used for the hole blocking film 84.

The lower electrode 90 is plurally formed, spaced apart in the form of a grid (matrix), with one lower electrode 90 corresponding to one pixel. Each lower electrode 90 is connected to a thin film transistor (hereinafter referred to simply as a TFT) 98 and an storage capacitor 96 of a signal output section 94. An insulating film 92 is provided between the signal output sections 94 and the lower electrodes 90, and the signal output sections 94 are formed on an insulating substrate 93. The insulating substrate 93 is preferably an electrically insulative thin substrate (a substrate with a thickness of the order of tens of microns) with low absorption of the radiation X and flexibility, in order to allow the radiation X to be absorbed at the radiation conversion layer 74. Specifically, it is preferable if the insulating substrate 93 is an artificial resin, an aramid, bionanofibers, film-form glass that can be wound into a roll (ultra-thin sheet glass), or the like.

Each signal output section 94 is formed with the storage capacitor 96, which corresponds with the lower electrode 90 and accumulates charges that have migrated to the lower electrode 90, and the TFT 98, which is a switching element that converts the charges accumulated at the storage capacitor 96 to electronic signals and outputs the electronic signals. A region in which the storage capacitor 96 and the TFT 98 are formed includes a region that overlaps with the lower electrode 90 in plan view. To minimize a planar area of the radiation detector 26 (the pixels), it is desirable if the region in which each storage capacitor 96 and TFT 98 are formed is completely covered by the lower electrode 90.

The radiation detector 26 may be of a penetration side sampling (PSS) type or of an irradiation site sampling (ISS) type. PSS is a system in which, as shown in FIG. 2, the radiation X is irradiated from the side of the radiation detector 26 at which the radiation conversion layer 74 is formed and the radiation detector 26 acquires the radiation image with the TFT substrate 70 that is provided at a rear face side relative to the face at which the radiation X is incident. In the radiation detector 26 in this case, light is more strongly emitted from the side of the radiation conversion layer 74 that is at the upper face side in FIG. 2. On the other hand, ISS is a system in which the radiation X is irradiated from the side of the radiation detector 26 at which the TFT substrate 70 is formed and the radiation detector 26 acquires the radiation image with the TFT substrate 70 that is provided at the rear face side relative to the face at which the radiation X is incident. In the radiation detector 26 in a case of ISS, radiation X that has passed through the TFT substrate 70 is incident on the radiation conversion layer 74 and light is more strongly emitted from the side of the radiation conversion layer 74 at which the TFT substrate 70 is disposed. Charges are generated by the light produced by the radiation conversion layer 74 in photoelectric conversion sections 87 of pixels 100 provided at the TFT substrate 70. Therefore, in a case in which the radiation detector 26 is configured for ISS, light emission positions of the radiation conversion layer 74 are closer to the TFT substrate 70 than in a case in which the radiation detector 26 is configured for PSS, as a result of which the resolution of the radiation images obtained by imaging is higher.

Figure 3:
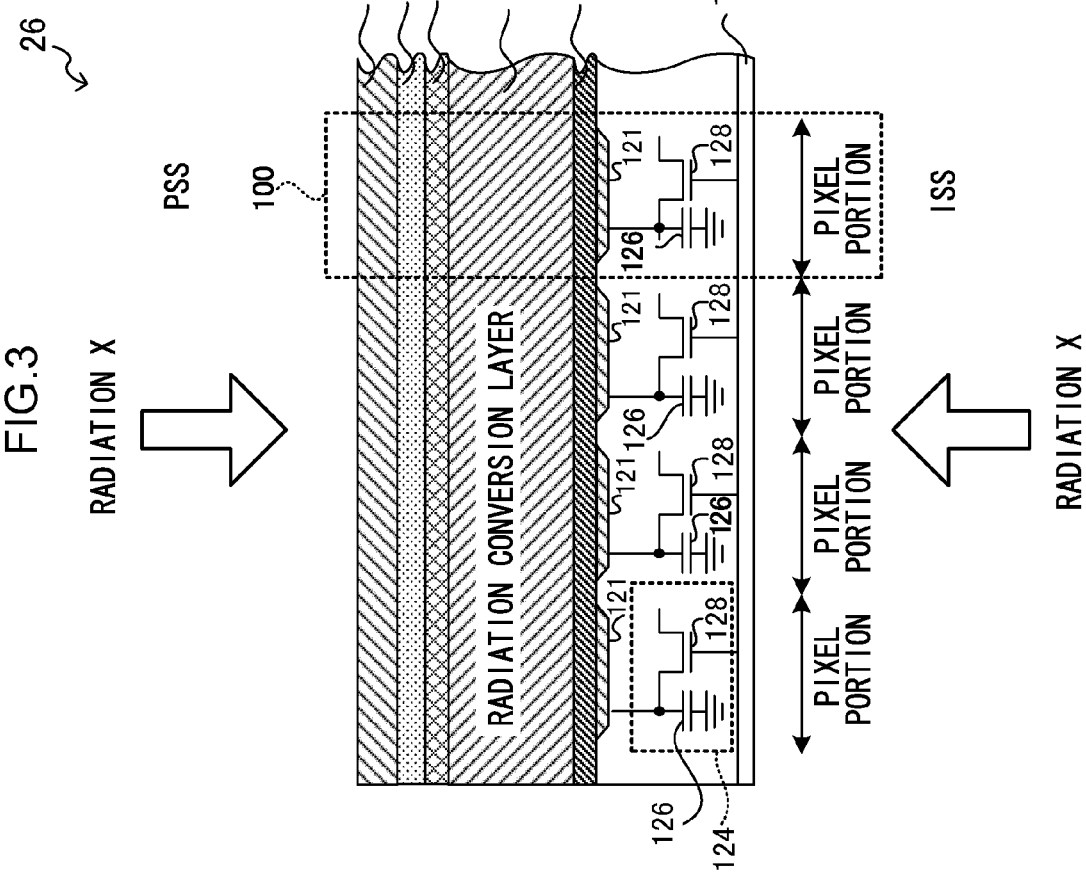
FIG. 3 is a schematic diagram showing an outline of a cross section of an example of a direct conversion-type radiation detector in accordance with the first exemplary embodiment.

The radiation detector 26 may instead be a direct conversion type of the radiation detector 26, as illustrated by the schematic view of a cross section of an example in FIG. 3. Similarly to the indirect conversion type described above, the radiation detector 26 shown in FIG. 3 is provided with a TFT substrate 110 and a radiation conversion layer 118.

The TFT substrate 110 has a function for collecting and reading out (detecting) carriers (holes), which are charges generated by the radiation conversion layer 118. The TFT substrate 110 is provided with an insulating substrate 122 and signal output sections 124. In a case in which the radiation detector 26 is an electron-reading sensor, the TFT substrate 110 has a function for collecting and reading out electrons.

The insulating substrate 122 is preferably an electrically insulative thin substrate (a substrate with a thickness of the order of tens of microns) with low absorption of the radiation X and flexibility, in order to allow the radiation X to be absorbed at the radiation conversion layer 118. Specifically, it is preferable if the insulating substrate 122 is an artificial resin, an aramid, bionanofibers, film-form glass that can be wound into a roll (ultra-thin sheet glass), or the like.

A signal detection portion 85 is provided with an storage capacitor 126, a TFT 128 and a charge collection electrode 121. The storage capacitor 126 is a charge storage capacitor. The TFT 128 is a switching element that converts charges accumulated at the storage capacitor 126 to electronic signals and outputs the electronic signals.

The charge collection electrodes 121 are plurally formed, spaced apart in the form of a grid (matrix), with one charge collection electrode 121 corresponding to one pixel. Each charge collection electrode 121 is connected to the TFT 128 and the storage capacitor 126.

The storage capacitor 126 has a function for accumulating charges (holes) collected by the charge collection electrode 121. The charges accumulated at the storage capacitor 126 are read out by the TFT 128. Thus, a radiation image is imaged by the TFT substrate 110.

An undercoat layer is formed between the radiation conversion layer 118 and the TFT substrate 110. With regard to reducing dark currents and leakage currents, the undercoat layer preferably has a rectifying characteristic. Accordingly, a resistivity of the undercoat layer is preferably at least $10^8$ $\Omega\cdot$cm, and a film thickness of the undercoat layer is preferably 0.01 μm to 10 μm.

The radiation conversion layer 118 is a photoconductive material that absorbs the irradiated radiation X and generates positive and negative charges (electron-hole carrier pairs) in response to the radiation. The radiation conversion layer 118 that is a photoelectric conversion layer preferably has amorphous selenium (a-Se) as a principal constituent. The radiation conversion layer 118 may use one or more of the following as a principal constituent: $Bi_2MO_{20}$ (M being Ti, Si or Ge), $Bi_4M_3O_{12}$ (M being Ti, Si or Ge), $Bi_2O_3$, $BiMO_4$ (M being Nb, Ta or V), $Bi_2WO_6$, $Bi_{24}B_2O_{39}$, ZnO, ZnS, ZnSe, ZnTe, $MNbO_3$ (M being Li, Na or K), PbO, $HgI_2$, $PbI_2$, CdS, CdSe, CdTe, $BiI_3$, GaAs, and the like. It is preferable if the radiation conversion layer 118 is a non-crystalline (amorphous) material that exhibits high resistance and excellent photoconductivity of irradiations of radiation, and that can be formed into films with large areas at low temperatures by vacuum deposition.

As an example, in a case in which the photoconductive material has a-Se as a principal constituent as in the present exemplary embodiment, the thickness of the radiation conversion layer 118 is preferably in a range from 100 μm to 2000 μm. In particular, the thickness is preferably in a range from 100 μm to 250 μm for mammography applications, and in a range from 500 μm to 1200 μm for general imaging applications.

An electrode interfacial layer 116 has a function for blocking injections of holes and a function for preventing crystallization. The electrode interfacial layer 116 is formed between the radiation conversion layer 118 and an overcoat layer 114. The electrode interfacial layer 116 is preferably an inorganic material such as CdS, $CeO_2$, $Ta_2O_5$, SiO or the like, or an organic polymer. For a layer formed of an inorganic material, it is preferable to use a composition in which carrier selectivity is adjusted by altering the composition from a stoichiometric composition or forming a multi-element composition with two or more compositions of elements in the same family. For a layer formed of an organic polymer, a composition in which a low-molecular electron transport material is mixed, in a weight ratio of 5% to 80%, into an insulating polymer such as a polycarbonate, polystyrene, polyimide, polycycloolefin or the like may be used. This electron transport material is preferably a material in which a carbon cluster is mixed, such as trinitrofluorene or a derivative thereof, a diphenoquinone derivative, a bis-naphthylquinone derivative, an oxazole derivative, a triazole derivative, $C_{60}$ (a fullerene), $C_{70}$ or the like. Specifically, TNF, DMDB, PBD and TAZ can be mentioned. Alternatively, a thin, insulative polymer layer may be preferably used. The insulative polymer layer is preferably, for example, parylene, polycarbonate. PVA, PVP, PVB, polyester resin, or an acrylic resin such as polymethyl methacrylate or the like. In this case, the film thickness is preferably not more than 2 μm, and more preferably not more than 0.5 μm.

The overcoat layer 114 is formed between the electrode interfacial layer 116 and a bias electrode 112. With regard to reducing dark currents and leakage currents, the overcoat layer 114 preferably has a rectifying characteristic. Accordingly, a resistivity of the overcoat layer 114 is preferably at least $10^8$ $\Omega\cdot$cm, and a film thickness of the overcoat layer 114 is preferably 0.01 μm to 10 μm. The bias electrode 112 is substantially the same as the bias electrode 72 of the direct conversion-type configuration described above, and has a function of applying a bias voltage to the radiation conversion layer 118.

The radiation detector 26 is not limited to the configurations shown in FIG. 2 and FIG. 3; various modifications are possible. For example, in a case of PSS, probabilities of the radiation X reaching the radiation detector 26 are lower. Thus, in each signal output section (94 or 124), instead of the configuration described above, another imaging component such as a complementary metal oxide semiconductor (CMOS) image sensor or the like with low resistance to the radiation X may be combined with the TFT. Further, a charge-coupled device (CCD) image sensor that shifts charges in accordance with shift pulses corresponding to TFT gate signals may be substituted.

As another example, a flexible substrate may be used. Ultra-thin plate glass formed by a recently developed float process may be used as a base material for a flexible substrate, and is preferable in terms of improving transmissivity of the radiation X. An ultrathin plate glass that may be used in this case is disclosed in, for example, "Floutohou niyoru sekai saihaku 0.1 mili-atsu no chouhaku itagarasu no kaihatsu ni seikou" (Successful development of the world's thinnest ultra-thin plate glass. 0.1 mm thick, by a float process"), Asahi Glass Co., Ltd. (online: accessed Aug. 20, 2011, URL: http://www.agc.com/news/2011/0516.pdf).

Figure 4:
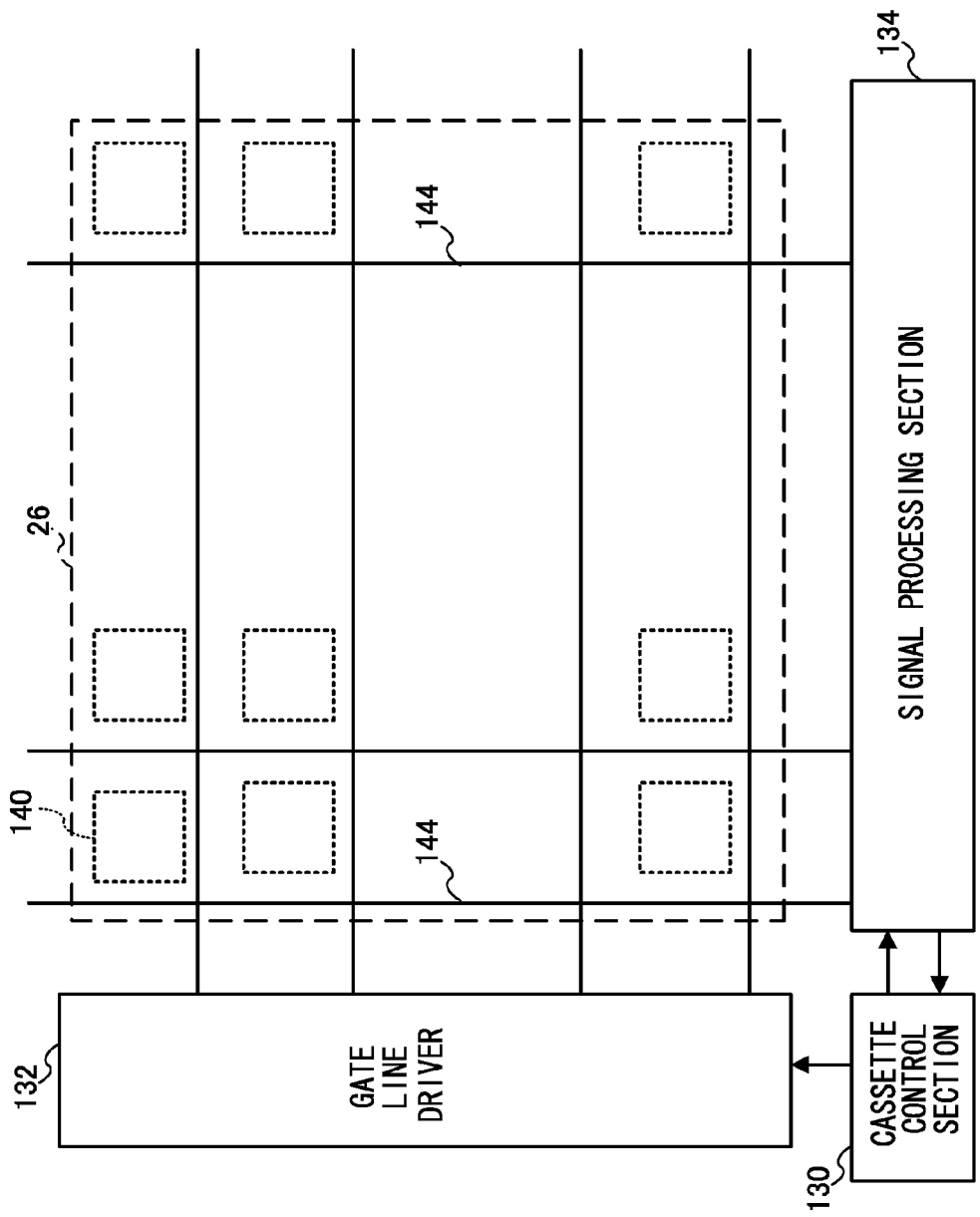
FIG. 4 is a circuit configuration diagram showing an outline of an example of an electronic cassette in accordance with the first exemplary embodiment.

Now, the circuit configuration of the electronic cassette 20, which is a radiation imaging device equipped with the above-described radiation detector 26 according to the exemplary embodiment, is described. FIG. 4 shows a circuit configuration diagram of an example of the configuration of the electronic cassette 20. In the following descriptions, as a concrete example, the electronic cassette 20 equipped with the radiation detector 26 shown in FIG. 2 is described. FIG. 4 shows a state in which the electronic cassette 20 is seen in a plan view from the side from which the radiation X is irradiated. The radiation conversion layer 74 is not shown in the drawing of FIG. 4.

The electronic cassette 20 is provided with a cassette control section 130, a gate line driver 132, a signal processing section 134, and a plural number of the pixels 100 (as a concrete example, n pixels in the present exemplary embodiment) that are arranged in a matrix pattern in row and column directions. The electronic cassette 20 is provided with plural gate lines 136 running along the row direction of the pixels 100, and is provided with plural signal lines 138 running along the column direction of the pixels 100. The gate lines 136 are connected to the gate line driver 132, and the signal lines 138 are connected to the signal processing section 134.

In the electronic cassette 20, the radiation X is converted to fluorescence by the radiation conversion layer 74, charges converted from the fluorescence by the photoelectric conversion film 86 are accumulated at the storage capacitors 96, and the charges may be read out as electronic signals by the TFTs 98 being sequentially turned ON row by row. Specifically, on-signals are sequentially outputted from the gate line driver 132 to the gate lines 136 in accordance with a predetermined frame rate (and gate-on duration). Thus, gate voltages are applied to the gates of the TFTs 98 and the TFTs 98 are sequentially turned on, in which state electronic signals corresponding to the accumulated charges respectively flow into the signal lines 138.

Figure 5:
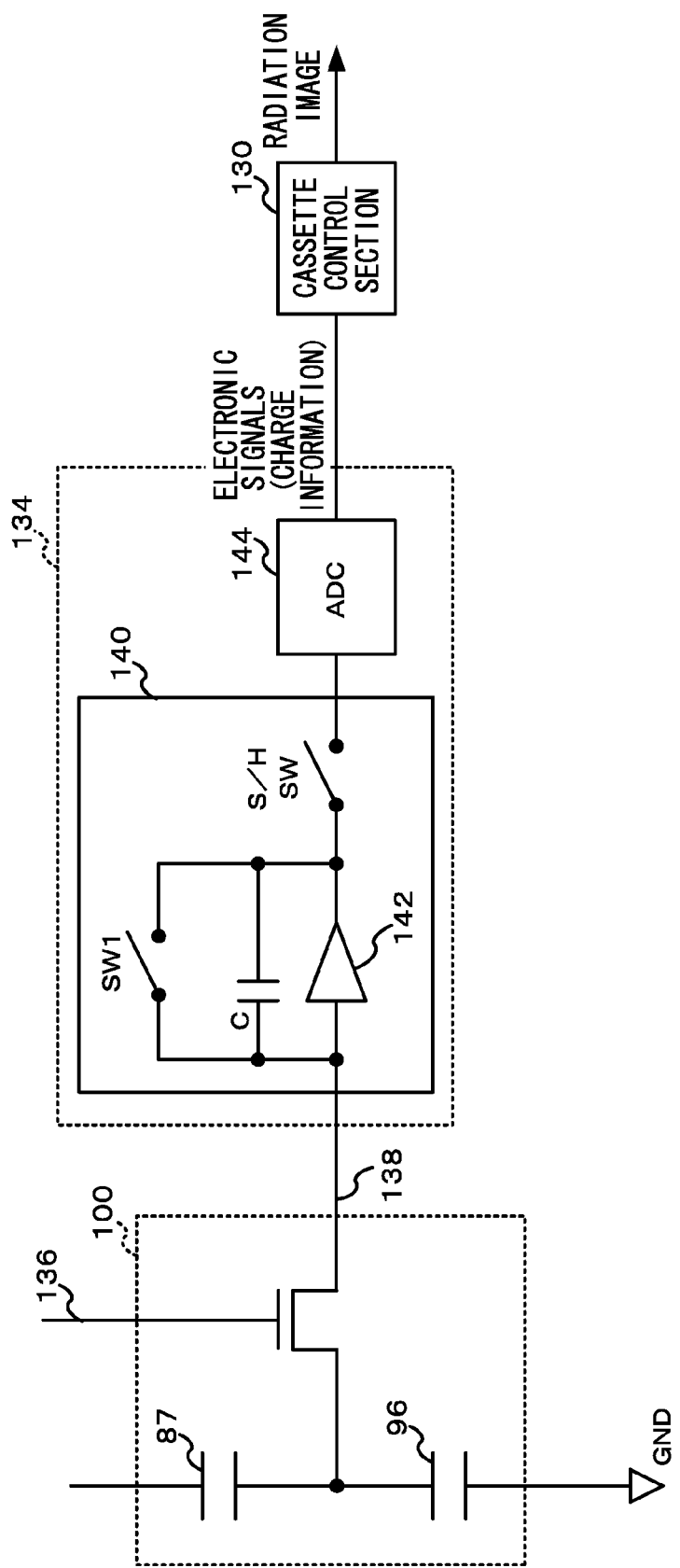
FIG. 5 is a schematic configurational diagram of an example of a signal processing section in accordance with the first exemplary embodiment

The charges (electronic signals) flowing into the signal lines 138 flow to the signal processing section 134. A schematic configurational diagram of an example of the signal processing section 134 is shown in FIG. 5. The signal processing section 134 amplifies inflowing charges (analog electronic signals) with amplification circuits 140, then performs analog-to-digital (A/D) conversion with an analog-to digital-converter (ADC) 144, and outputs the electronic signals that have been converted to digital signals to the cassette control section 130. Although not shown in FIG. 5, the amplification circuits 140 are provided one for each of the signal lines 138. That is, the signal processing section 134 includes the plural amplification circuits 140 in the same number as the number of signal lines 138 in the radiation detector 26.

Each amplification circuit 140 is configured as a charge amplifier circuit. The amplification circuit 140 is provided with an amplifier 142 such as an operational amplifier or the like, a capacitor C connected in parallel with the amplifier 142, and a switch for charge resetting SW1 connected in parallel with the amplifier 142. In a case in which the switch for charge resetting SW of the amplification circuit 140 is in the OFF state, charges (electronic signals) are read from the TFT 98 of a pixel 100, the charges read from the TFT 98 are integrated at the capacitor C, and a voltage value outputted from the amplifier 142 in accordance with the integrated charge amount is amplified.

The cassette control section 130 applies charge reset signals to the switches for charge resetting SW1 and performs control to turn the switches for charge resetting SW1 ON and OFF. In a case in which a switch for charge resetting SW1 is in the ON state, the input side and output side of that amplifier 142 are short-circuited and charges are discharged from the capacitor C.

The ADC 144 has a function for converting electronic signals that are analog signals inputted from the amplification circuits 140 to digital signals, in a case in which sample-and-hold (S/H) switches SW are in the ON state. The ADC 144 sequentially outputs the electronic signals that have been converted to digital signals to the cassette control section 130.

The electronic signals outputted from all the amplification circuits 140 provided in the signal processing section 134 are inputted to the ADC 144 according to the present exemplary embodiment. That is, the signal processing section 134 according to the present exemplary embodiment includes a single ADC 144 regardless of the number of amplification circuits 140 (and signal lines 138).

Figure 6:
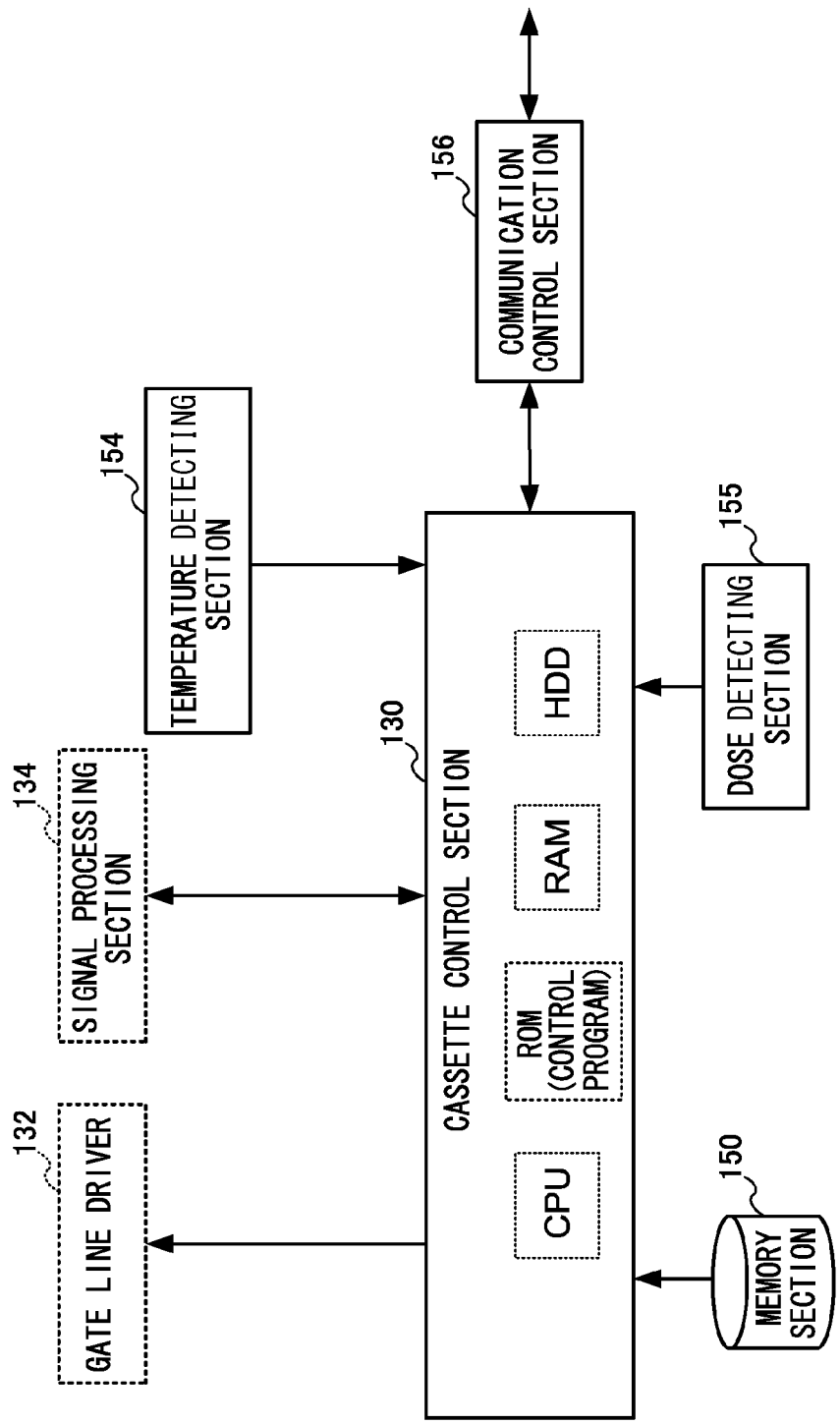
FIG. 6 is a functional block diagram of an example of configurations that correspond to the functions of a cassette control section in the electronic cassette in accordance with the first exemplary embodiment.

The cassette control section 130 includes functions for controlling overall operations of the electronic cassette 20. The cassette control section 130 according to the present exemplary embodiment also has a function for, in a case in which a radiation image is being imaged, controlling periods of integration of charges at the capacitors C of the amplification circuits 140 and timings at which the gates of the TFTs 98 are turned ON and OFF (described in detail herebelow). FIG. 6 shows a functional block diagram of an example of configurations corresponding to the functions of the cassette control section 130 of the electronic cassette 20 in accordance with the present exemplary embodiment.

The cassette control section 130 is provided with a CPU, ROM, RAM and an HDD. The CPU includes functions for controlling overall operations of the electronic cassette 20. Various programs including a control program to be used at the CPU and suchlike are pre-memorized in the ROM. The RAM includes functions for temporarily storing various kinds of data. The HDD includes functions for storing and retaining various kinds of data.

A communication control section 156 includes functions for exchanging various kinds of information, including image information of radiation images, with the radiation image processing device 14, the console 16 and suchlike by wireless communications and wired communications.

A temperature detecting section 154 has a function for detecting a temperature of the electronic cassette 20, more preferably a temperature of the radiation detector 26. The temperature detected by the temperature detecting section 154 is outputted to the cassette control section 130. The temperature detecting section 154 may be plurally provided at the radiation detector 26.

A dose detecting section 155 has a function for detecting a dose of the radiation X that is irradiated on the electronic cassette 20. The configuration of the dose detecting section 155 is not particularly limited, however, it is sufficient if the dose detecting section 155 can sense the radiation X irradiated on the electronic cassette 20 through a predetermined detecting period and compare the dose irradiated during the detecting period with a predetermined threshold, a profile or the like. The configuration of the dose detecting section 155 may be, for example, a configuration that is provided in the radiation detector 26 for detecting the radiation X, and some of the pixels 100 may be used as pixels for detecting. Pixels 100 in which the TFTs 98 are short-circuited or the like may be used as these pixels for detecting, but this is not a limitation. Further, a sensor that detects the dose may be provided separately. Further yet, in a case in which automatic exposure control (AEC) processing is applied at the electronic cassette 20 side during imaging to control operations for imaging of a radiation image, an AEC processing configuration may be used. The term "dose" as used in the present exemplary embodiment is intended to include a "mAs" value in which a tube current (mA) in a case in which the radiation X is being produced is multiplied by an irradiation duration (s).

The cassette control section 130 controls the radiation detector 26 so as to carry out imaging of a radiation image in accordance with an imaging menu, received by the communication control section 156, that includes imaging conditions for in a case in which a radiation image is being imaged and the like.

The cassette control section 130 controls ON and OFF timings of the TFTs 98 connected to the different gate lines 136 in accordance with a frame rate of the radiation image being imaged. In accordance with this control, ON states of the TFTs 98 connected to a number of different gate lines 136 in the electronic cassette 20 overlap, depending on the frame rate. The cassette control section 130 performs further control to set the integration periods of the capacitors C of the amplification circuits 140 and the ON and OFF timings of the TFTs 98, taking account of the frame rate, the type of video image and the like and, on the basis of temperatures detected by the temperature detecting section 154 and the like, the amplitudes and time constants of feedthrough components. In order to simplify the descriptions herebelow, a feedthrough component that is generated by the TFTs 98 connected to a given gate line 136 being turned OFF is referred to as "the feedthrough component (OFF)", and a feedthrough component that is generated by the TFTs 98 connected to a subsequent gate line 136 after the given gate line 136 being turned ON is referred to as "the feedthrough component (ON)".

In the present exemplary embodiment, the integration period of the capacitors C is set so as to encompass an integration period in which the feedthrough component (OFF) is integrated, and an integration period in which the feedthrough component (ON) and the charges read out from the storage capacitors 96 of the pixels 100 in accordance with the ON state are integrated. The cassette control section 130 controls the ON and OFF timings of the TFTs 98 in accordance with the set integration periods.

Now, the feedthrough components that arise in the radiation detector 26 are described. In a case in which numerous switching elements such as the TFTs 98 or the like are arranged in a two-dimensional pattern, as in the TFT active matrix substrate used in the radiation detector 26 according to the present exemplary embodiment, the plural gate lines for turning the switching elements ON and OFF and the plural signal lines for transferring the electronic signals from the pixels whose switching elements have been turned ON form an intersecting arrangement. Thus, parasitic capacitances occur. In the radiation detector 26, in a case in which a switching element is turned ON or is turned OFF, the amplitude of a voltage applied to the parasitic capacitance at the point of intersection between the gate line and the signal line that are connected to that switching element is changed. Consequently, induced charges are generated at the parasitic capacitance. The induced charges generated at the parasitic capacitance are superimposed on the charges being transferred through the signal line (signal charges for a radiation image) in the form of a noise component which is a signal (charges) referred to as a feedthrough component.

Figure 7:
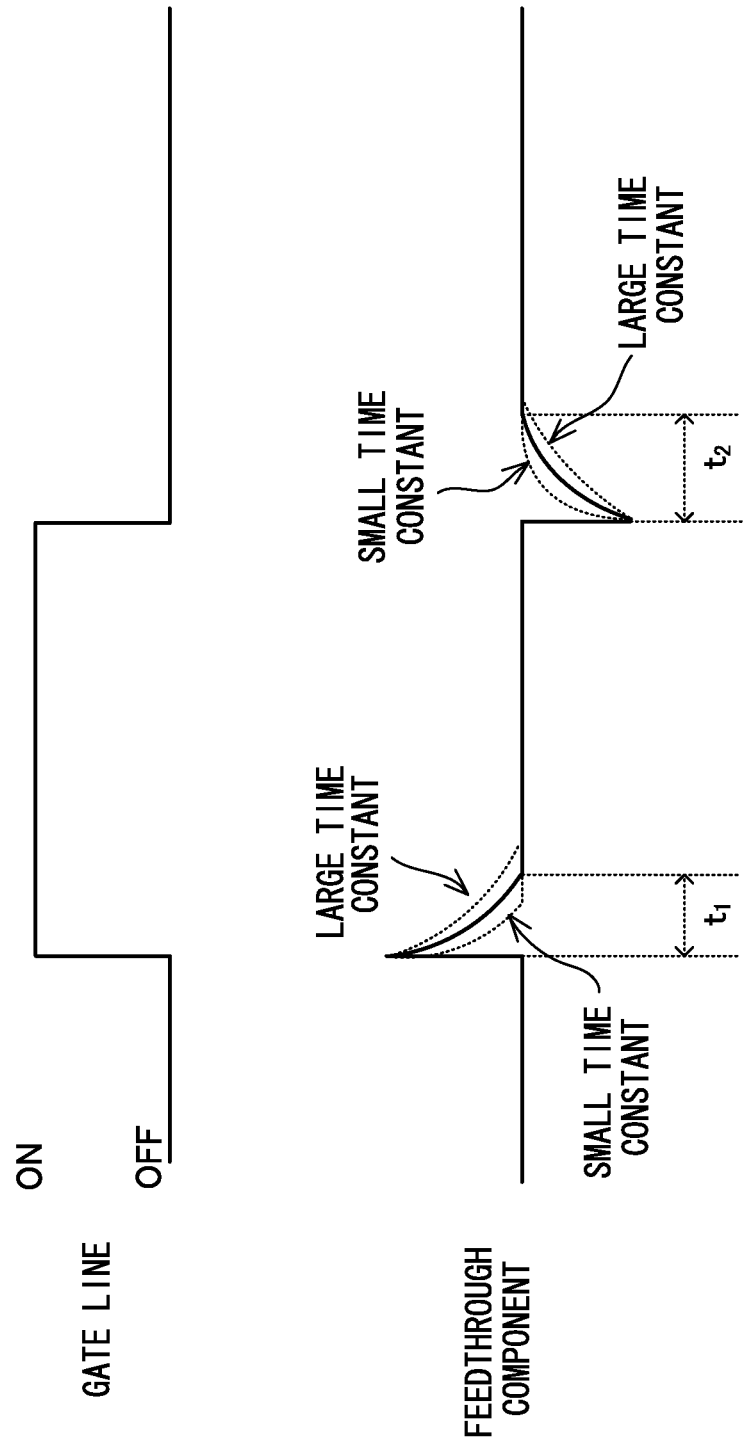
FIG. 7 is a descriptive diagram showing a relationship between on/off control of a switching element and generated feedthrough components in the electronic cassette in accordance with the first exemplary embodiment.

FIG. 7 shows a relationship between ON/OFF control of a switching element and the generated feedthrough components. Energy amounts (charge amounts) of the feedthrough component (ON) and the feedthrough component (OFF) are the same, but the feedthrough components differ between positive and negative, and differ in profile. As illustrated in FIG. 7, a generation period t2 of the feedthrough component (OFF) is longer than a generation period t1 of the feedthrough component (ON). The generation periods t1 and t2 of the feedthrough components (ON) and (OFF) differ depending on amplitudes and time constants of the feedthrough components.

Figure 8A:
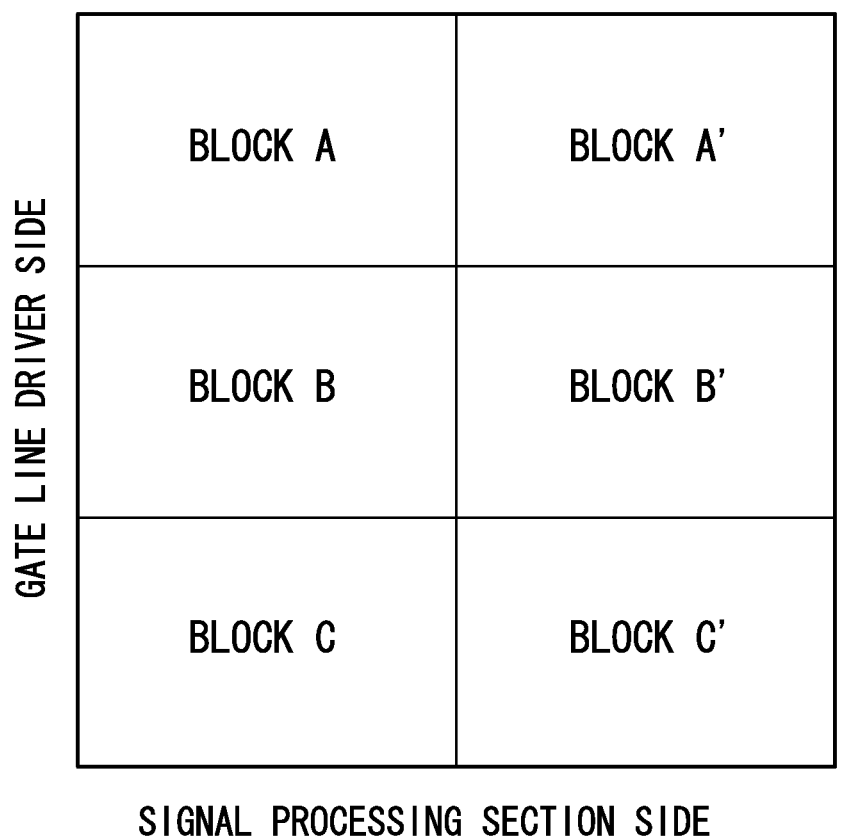
FIG. 8A is a descriptive diagram showing a specific example in which an area (region) of a radiation detector in accordance with the first exemplary embodiment on which radiation is irradiated is divided into a plural number of regions, showing a case of division into six regions (blocks A, A', B, B', C and C').
Figure 8B:
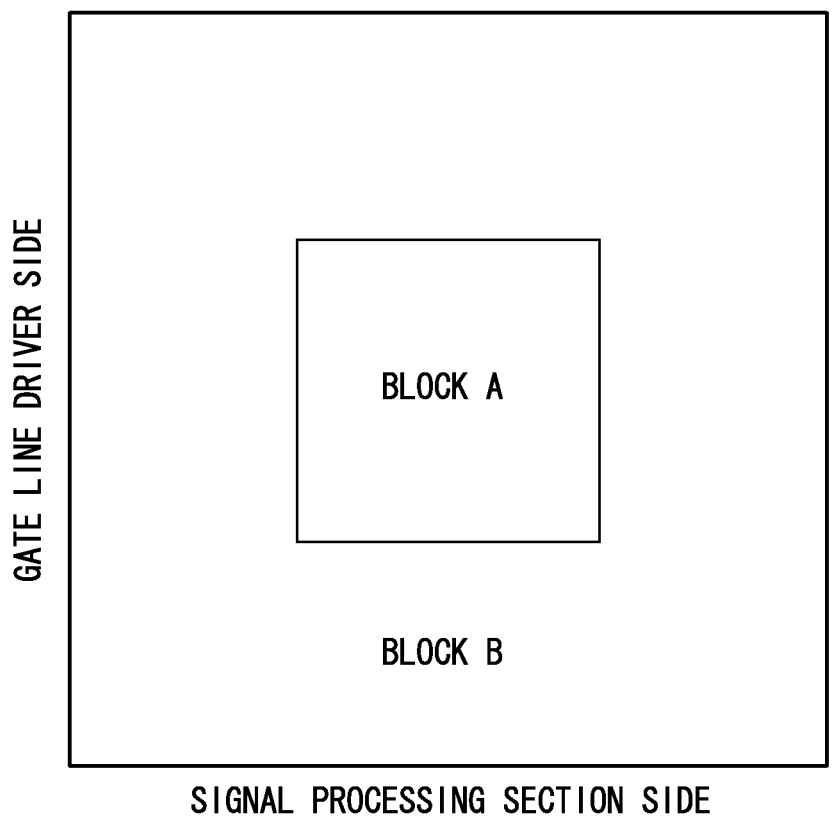
FIG. 8B is a descriptive diagram showing a specific example in which the area (region) of the radiation detector in accordance with the first exemplary embodiment on which radiation is irradiated is divided into a plural number of regions, showing a case of division into two regions: a central portion of the area on which radiation is irradiated (block A) and an outer edge portion (block B).

The amplitudes of the generated feedthrough components differ in accordance with the position of the TFT 98 in the radiation detector 26. In general, the longer the lengths of the gate lines 136 and the signal lines 138, the larger the feedthrough components. Specifically, in the present exemplary embodiment, the longer a sum of the length of the gate line 136 from the gate line driver 132 to the TFT 98 of a pixel 100 and the length of the signal line 138 from the signal processing section 134 to the TFT 98 of the pixel 100, the larger the feedthrough components. Accordingly, in the present exemplary embodiment, an area (region) of the radiation detector 26 on which the radiation X is irradiated is divided into a plural number of regions, and control is applied in accordance with the amplitudes of the feedthrough components in the respective divided regions. FIG. 8A and FIG. 8B show specific examples of these regions. FIG. 8A shows a case of division into six regions (blocks A, A', B, B', C and C'). In the case shown in FIG. 8A, the feedthrough component is largest in block A', which is furthest from the gate line driver 132 and the signal processing section 134, and the feedthrough component is smallest in block C, which is closest to the gate line driver 132 and the signal processing section 134, in the case shown in FIG. 8A.

Figure 9:
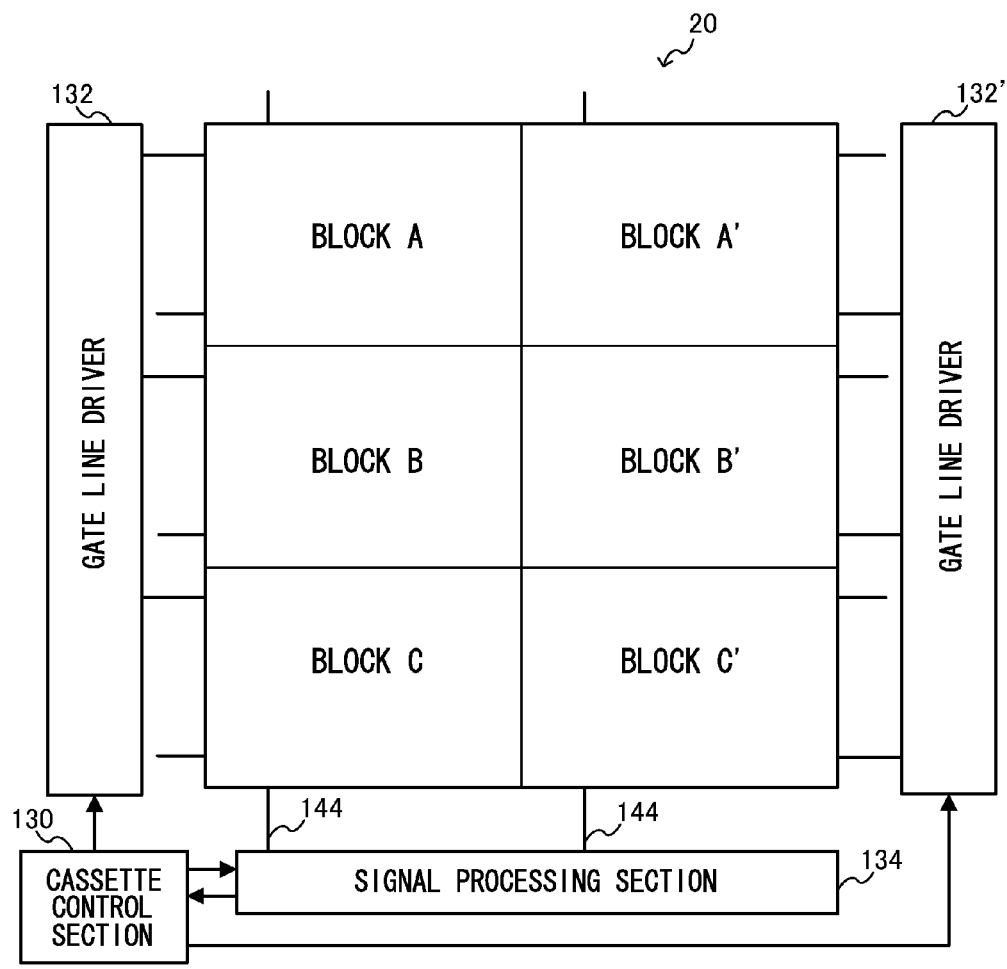
FIG. 9 is a circuit configuration diagram of an alternative example of the electronic cassette in accordance with the first exemplary embodiment.

In a case of division such that there are plural regions in the row direction, for example, the case shown in FIG. 8A, it is desirable, as shown in FIG. 9, to provide the gate line driver 132 to output gate signals to block A, block B and block C, and a gate line driver 132' to output gate signals to block A', block B' and block C'. In FIG. 9, the gate line driver 132 and the gate line driver 132' are configured as separate units, but the same may be configured as a single gate line driver.

FIG. 8B shows a case of division into two regions, a central portion of the area on which the radiation X is irradiated (block A) and an outer edge portion (block B). In general, imaging is performed such that a region of interest of the imaging subject 30 is disposed at a middle portion of the area on which radiation X is irradiated, such that the region of interest is imaged at the middle of the radiation image. Thus, in radiation images, higher image quality is required towards the central portion (block A). Therefore, it is preferable to set the regions in this manner in a case of applying control that distinguishes the central portion from other regions, such that the feedthrough component is controlled more appropriately. Note that, methods of dividing up the regions are not limited to the above.

In a case of division into plural regions as shown in FIG. 8A and FIG. 8B, it is preferable to provide the temperature detecting section 154 in each region or in each of predetermined regions, such that the respective temperatures thereof may be detected.

Figure 10:
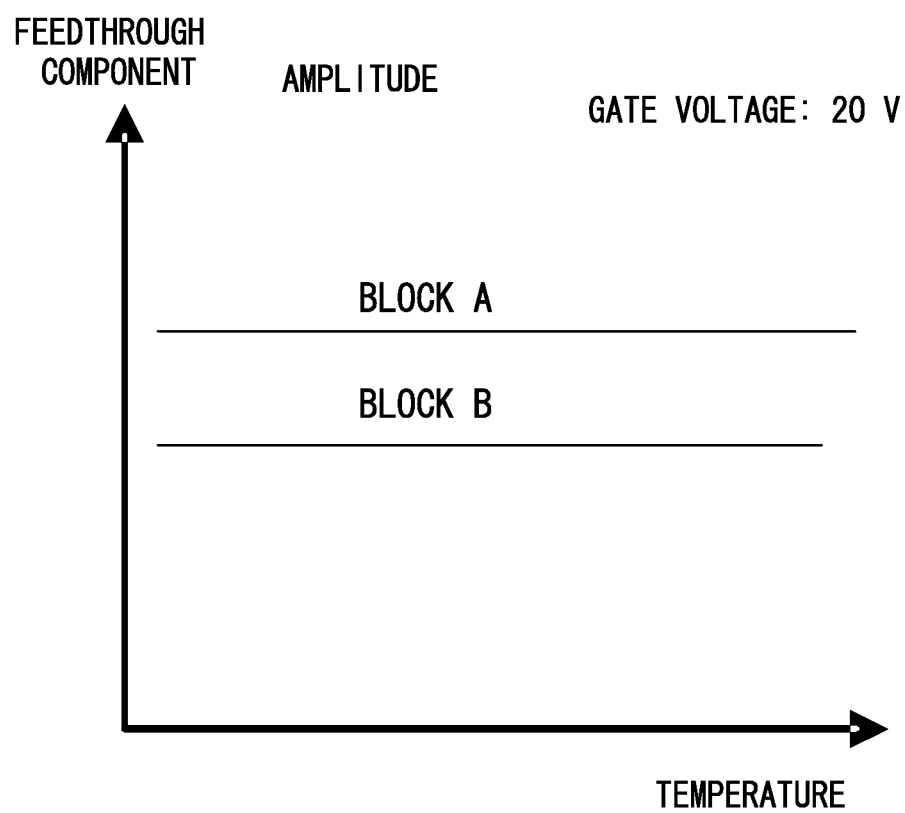
FIG. 10 is a descriptive diagram illustrating correspondences between the amplitudes of feedthrough components and temperature in the electronic cassette in accordance with the first exemplary embodiment.

FIG. 10 shows correspondences between the amplitudes of the feedthrough components and temperature. FIG. 10 illustrates, as an example, correspondences for block A and block B shown in FIG. 8A. The feedthrough components differ with the amplitudes of the voltages applied to the gates when the TFTs 98 are turned ON and OFF. Accordingly, in this case, the amplitudes of the feedthrough components are shown for 20 V, which is a gate voltage that is ordinarily applied in the present exemplary embodiment when reading from the storage capacitors 96 of the pixels 100.

Figure 11:
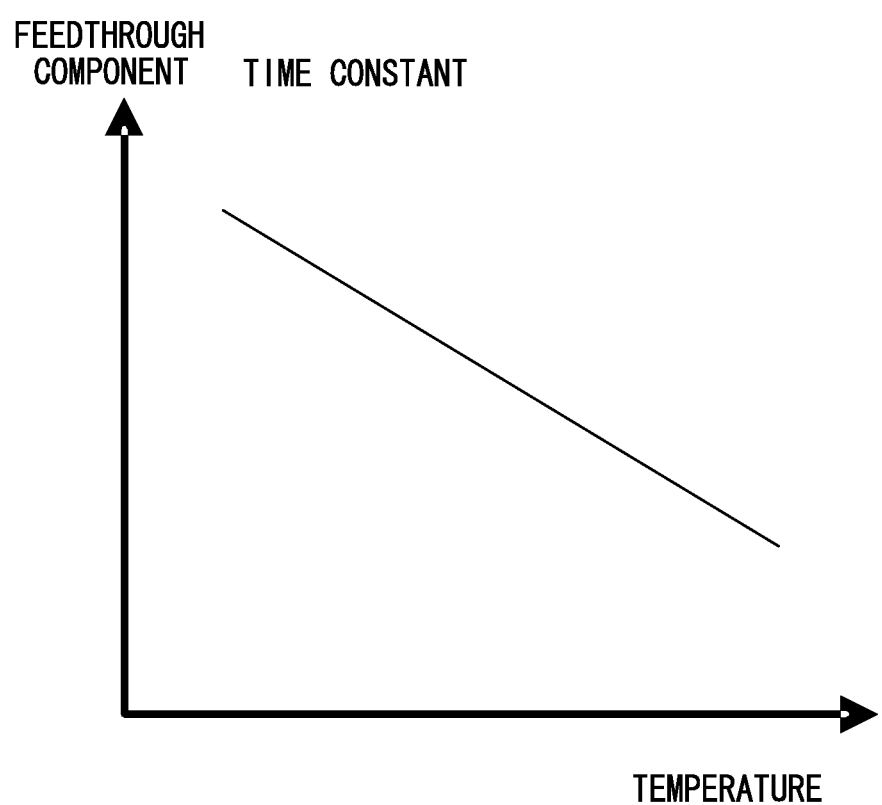
FIG. 11 is a descriptive diagram illustrating a correspondence between time constants of feedthrough components and temperature in the electronic cassette in accordance with the first exemplary embodiment.

FIG. 11 shows a correspondence between the time constants of the feedthrough components and temperature. In general, leakage currents in the TFTs 98 increase in a case in which the temperature of the radiation detector 26 is higher. Therefore, as shown in FIG. 11, the higher the temperature of the radiation detector 26, the smaller the time constants of the feedthrough components; and the smaller the time constants, the shorter the generation periods t1 and t2 as shown in FIG. 7.

In the present exemplary embodiment, a table representing the correspondences shown in FIG. 10 and FIG. 11 for each region (block) is memorized in a memory section 150 in advance. The amplitudes of the feedthrough components and the table may be prepared in advance on the basis of offset images (images that are imaged in a state in which the radiation X is not being irradiated) that are acquired with the ON and OFF timings of the TFTs 98 being arbitrarily set. For the amplitudes of the feedthrough components used in the table, an average value or a maximum value or the like of the TFTs 98 of the pixels 100 in each region (block) may be used. Which value is used is not particularly limited, and may differ between the regions.

In the electronic cassette 20 according to the present exemplary embodiment (the radiation detector 26), the charge amounts accumulated at the storage capacitors 96 of the individual pixels 100 are very small; the signal charges being transferred along the signal lines are of the same order as the order of the feedthrough components. Therefore, the effects of the feedthrough components cannot be disregarded. In particular, in a case of video imaging, the dose of each image is smaller than in still imaging. Therefore, the charge amounts accumulated at the storage capacitors 96 of the pixels 100 are small, and the effect of the feedthrough components may be larger. Therefore, in video imaging with small doses of the radiation X, it is necessary to suppress the effects of the feedthrough components.

Specifically, in the present exemplary embodiment, the effects of the feedthrough components may be suppressed by cancelling out a feedthrough component (ON) with a feedthrough component (OFF). Accordingly, in the electronic cassette 20, the integration period of the capacitors C of the amplification circuits 140 is set so as to encompass an integration period in which charges (signals) read out from a pixel 100 are integrated, the feedthrough component (ON) generation period t1, and the feedthrough component (OFF) generation period 2. Note that, in the present exemplary embodiment, the generation period t1 is considered to be equal to the integration period for integrating the feedthrough component (ON), and the generation period t2 is considered to be equal to the integration period for integrating the feedthrough component (OFF).

As a consequence of this specification, in a case in which the charges are being integrated at the capacitor C of an amplification circuit 140 in the electronic cassette 20, the feedthrough component (ON) is cancelled out by the feedthrough component (OFF). Therefore, in the electronic cassette 20, the feedthrough components that are superimposed on the charges (signals) read out from the pixels 100 may be suppressed.

In the present exemplary embodiment, in a case in which the feedthrough components (ON) are to be cancelled out by the feedthrough components (OFF), driving waveforms of the TFTs 98 are shifted in accordance with the frame rate, within a range such that reset periods can be assured, and the ON states of the TFTs 98 connected to different gate lines 136 are caused to overlap (described in detail below).

In a case in which the ON states of plural TFTs 98 are overlapped in this manner, a reading period (described in detail below) of the electronic cassette 20 may be shortened, and an increase in the frame rate may be enabled.

In imaging of video images, a higher frame rate is sometimes required. For example, in video imaging in general, 15 fps is said to be adequate for images of the digestive system, 30 fps is considered adequate for images of the circulatory system, and 60 fps is considered adequate for images of children. However, with higher frame rates up to, for example, 120 fps or the like, movements of the heart and the like may be smoothly seen. In particular, a frame rate of the order of 120 fps is preferable for imaging the heart of a child. Moreover, in imaging using a radiocontrast agent, tracing may be possible with a smaller amount of the radiocontrast agent in a case in which the frame rate is higher. Using smaller doses of radiocontrast agents is preferable, because radiocontrast agents may cause side effects.

In general, an upper limit on the integration period of the capacitors C of the amplification circuits 140 is governed by the frame rate. In a case of imaging at a high frame rate, an imaging duration for each frame is shorter than in a case of imaging at a low frame rate, and the integration period of the capacitors C of the amplification circuits 140 is shorter. In a case in which the integration period is longer, there is a higher degree of freedom in control of the ON and OFF timings of the TFTs 98 to encompass the feedthrough component (ON) generation period t1 and the feedthrough component (OFF) generation period t2 in the integration period. For example, even in a case in which the generation period t1 and the generation period t2 do not overlap, the feedthrough component (ON) and the feedthrough component (OFF) may cancel out. That is, even in a case in which a period in which the TFTs 98 connected to the gate line 136 of a given row are turned ON and a period in which the TFTs 98 connected to the gate line 136 of the subsequent row after the given row are turned ON do not overlap, the feedthrough components may be able to cancel out.

On the other hand, in a case in which the integration period is short, there is a lower degree of freedom of control of the ON and OFF timings of the TFTs 98, and the generation period t1 and generation period t2 must overlap to a significant extent. In this case, the ON and OFF timings of the TFTs 98 must be controlled such that, for example, whichever period is longer of the generation period t1 and the generation period t2 may completely encompass the shorter period. That is, an overlap period T, in which the period in which the TFTs 98 connected to the gate line 136 of a given row are turned ON and the period in which the TFTs 98 that are driven subsequently are turned ON overlap, must be more strictly controlled.

Thus, in consideration of these facts, in order to suppress the feedthrough components in imaging at a high frame rate in the electronic cassette 20 according to the present exemplary embodiment, in a case in which the frame rate is above a predetermined threshold (a high frame rate): a temperature is acquired from the aforementioned temperature detecting section 154; the amplitudes and time constants of the feedthrough components corresponding to the acquired temperature are acquired from the table memorized in the memory section 150; and the ON and OFF timings of the TFTs 98 are controlled accordingly.

The specification of the integration period of the capacitors C of the amplification circuits 140 and control of the ON and OFF timings of the TFTs 98 in the electronic cassette 20 according to the present exemplary embodiment, in accordance with the feedthrough components, are described in detail with reference to the attached drawings.

Figure 12:
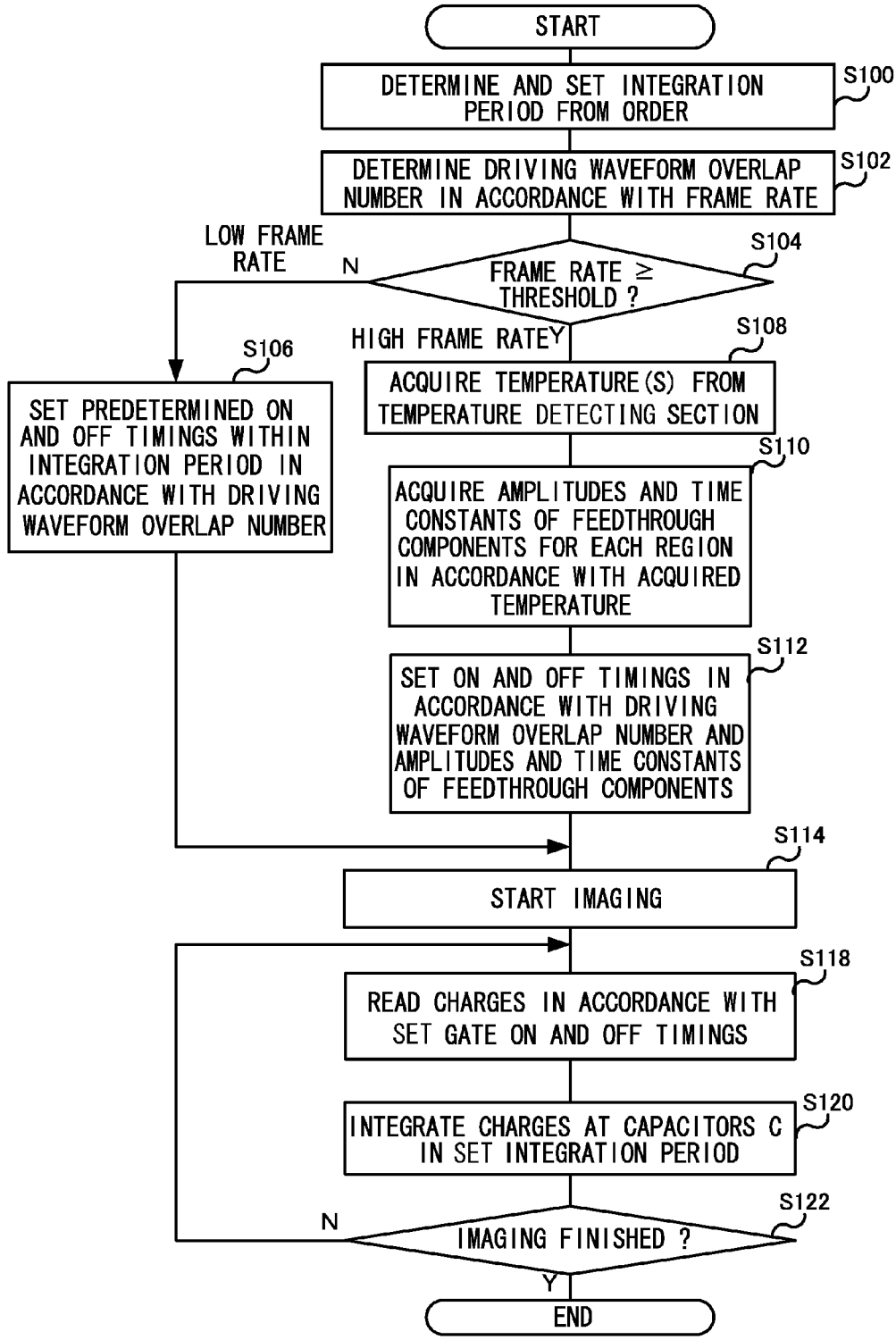
FIG. 12 is a flowchart showing an example of control processing in a case of switching control of ON and OFF timings of a TFT in accordance with a frame rate in the electronic cassette in accordance with the first exemplary embodiment.

First, control processing in a case in which control of the ON and OFF timings of the TFTs 98 is switched in accordance with the frame rate is described. FIG. 12 shows a flowchart of an example of this control processing in the present exemplary embodiment. This control processing of the present exemplary embodiment is carried out by a control processing control program being executed by the CPU of the cassette control section 130. In the present exemplary embodiment, this control program is memorized in advance in the ROM of the cassette control section 130, or the memory section 150 or the like. Configurations are also possible in which the control program is downloaded from an external system (the RIS) or a CD-ROM, or via USB or the like.

The present control processing is executed in a case in which an order representing imaging conditions is received by the communication control section 156 and imaging of a radiation image is commanded. First, in step S100, the integration period of the capacitors C of the amplification circuits 140 is determined from the acquired order, and the determined integration period is set as the charge integration period of the capacitors C of the amplification circuits 140. In the present exemplary embodiment, the frame rate is included in the order. In general, an upper limit for the integration period is established from the frame rate. In the present exemplary embodiment, however, the integration period is set to a duration determined in advance for each frame rate in accordance with the specifications of the electronic cassette 20 (the radiation detector 26), taking account of the feedthrough components.

In the present exemplary embodiment, because plural driving waveforms of the TFTs 98 are overlapped, a reset period (for each gate line 136) of the TFTs 98 (including an ADC period of the amplification circuits 140 and a reset period of integrated charges) is shortened within a range that does not cause problems for imaging. The reset period of the amplification circuits 140 may be shortened because the charges integrated at the capacitors C are sequentially transferred in pipeline processing.

Then, in step S102, a number of driving waveforms to be overlapped is determined in accordance with the frame rate acquired from the order. In the present exemplary embodiment, this overlap number is determined in accordance with the frame rate as mentioned above, the integration period and the reset period. Larger overlap numbers correspond with higher frame rates. In the present exemplary embodiment, in a case with a low frame rate, a number of driving waveforms caused to overlap is smaller than with a high frame rate. However, a case with a low frame rate is not limited thus. For example, configuration is possible such that driving waveforms (feedthrough components) are used for neighboring gate lines 136 rather than plural driving waveforms being caused to overlap.

In step S104, a determination is made as to whether the frame rate is above a threshold. In the present exemplary embodiment, the threshold that defines high frame rates is determined and memorized in the memory section 150 or the like in advance. In this step, in a case in which the result of the comparison with the threshold is negative, the frame rate is a low frame rate, and accordingly the CPU proceeds to step S106.

In step S106, the ON and OFF timings of predetermined TFTs 98 are set such that the generation periods t1 and t2 according to the determined overlap number are completely encompassed within the set integration periods. Then the CPU proceeds to step S114. In the present exemplary embodiment, the ON and OFF timings of the TFTs 98 in this case are determined in advance in accordance with the specifications of the radiation detector 26, image qualities of radiation images and so forth. A timing at which TFTs 98 are turned ON is ordinarily determined in accordance with the frame rate. Therefore, in the present exemplary embodiment, it is the timing at which the TFTs 98 are turned OFF that is adjusted.

On the other hand, in a case in which the result of the determination in step S104 is that the frame rate is above the threshold, this is a high frame rate, and accordingly, the CPU proceeds to step S108. In step S108, the temperature(s) of the radiation detector 26 is/are acquired from the temperature detecting section 154. A method of acquisition of temperature from the temperature detecting section 154 may be, for example, detecting the temperature of each region with the temperature detecting section 154 and acquiring the temperature for each region from the temperature detecting section 154. Alternatively, the temperature at a predetermined region may be detected by the temperature detecting section 154 and the temperature of each region estimated from the detected temperature. Further, temperature characteristics of the radiation detector 26 may be ascertained in advance, and the temperature of each region estimated on the basis of the temperature characteristics and a temperature detected by the temperature detecting section 154. This acquisition method is not particularly limited, but it is preferable to acquire or estimate a temperature for each region.

In step S110, in accordance with the acquired temperatures, the amplitudes and time constants of the feedthrough components in each region (block) are looked up in the table memorized in the memory section 150 and acquired therefrom.

In step S112, depending on the driving waveform overlap number and the acquired feedthrough component amplitudes and time constants, the ON and OFF timings of the TFTs 98 are set. In the present exemplary embodiment, relationships between these feedthrough component amplitudes and time constants and the generation periods t1 and t2 are obtained in advance and memorized in the memory section 150. On the basis thereof, the ON and OFF timings of the TFTs 98 and an overlap period T of the on-periods are set (see FIG. 13).

Figure 13:
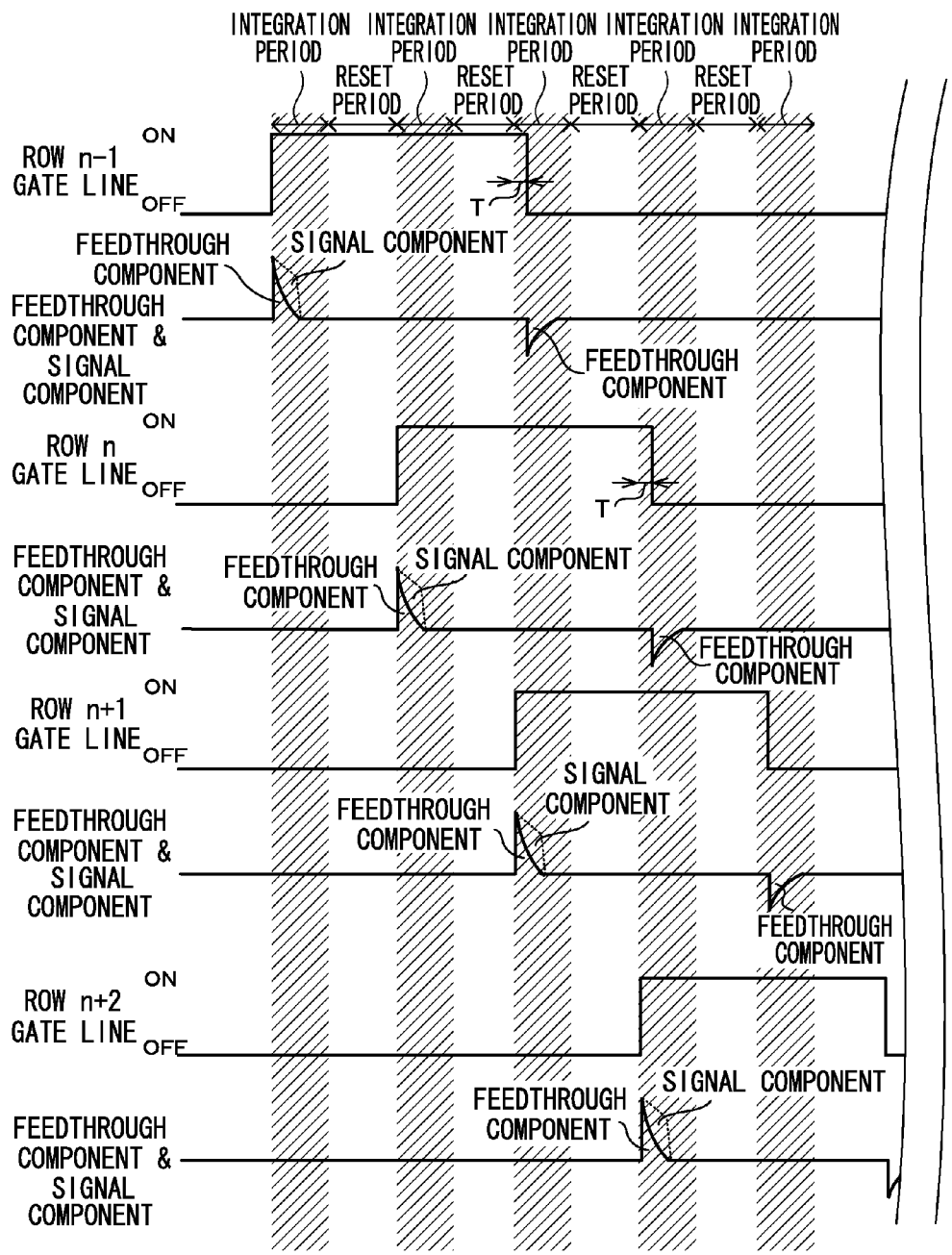
FIG. 13 is a timing chart of an example of a case of imaging at a low frame rate in the control processing of the electronic cassette in accordance with the first exemplary embodiment.
Figure 14:
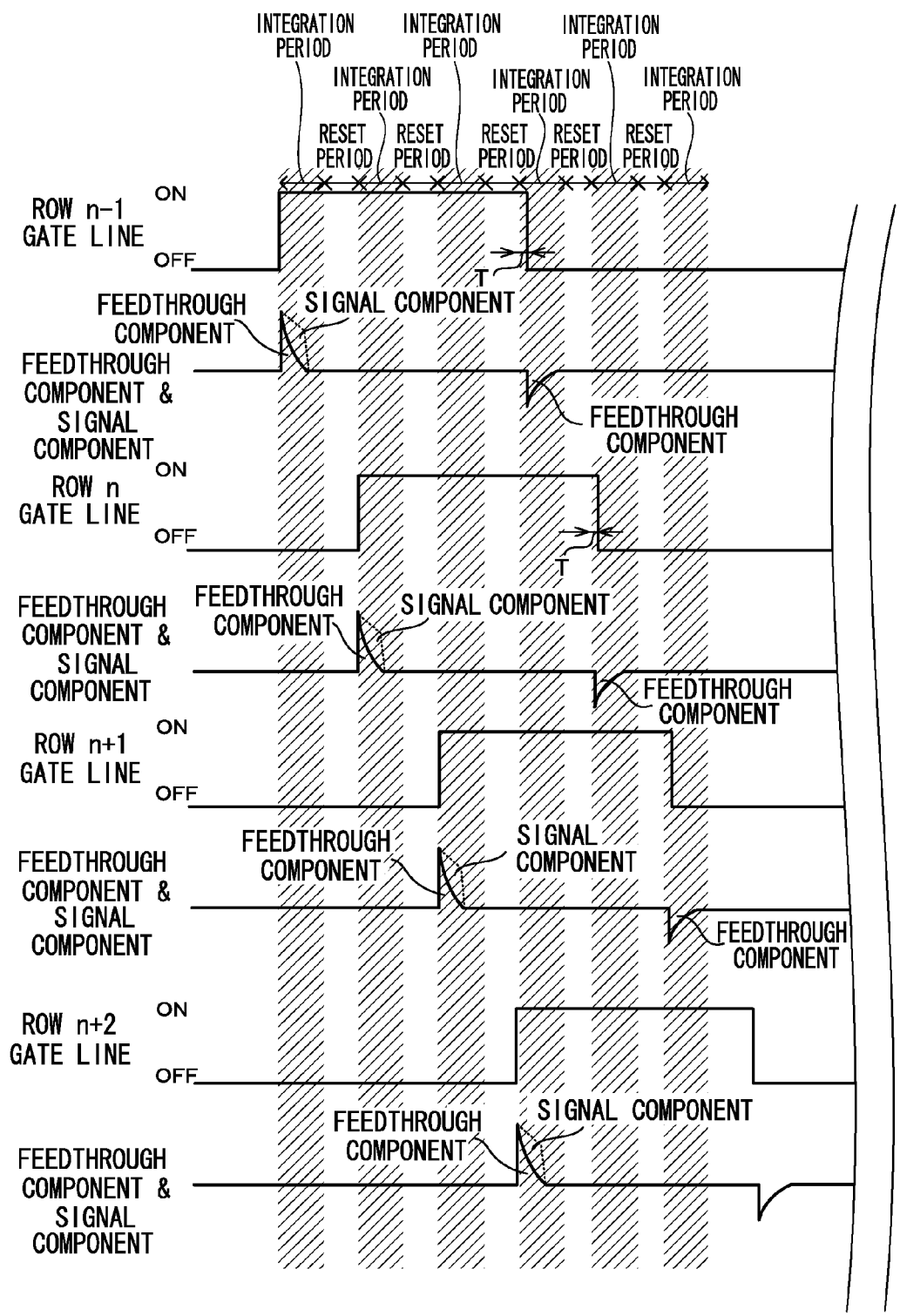
FIG. 14 is a timing chart of an example of a case of imaging at a high frame rate in the control processing of the electronic cassette in accordance with the first exemplary embodiment.

In step S114, in a case in which an irradiation of the radiation X from the radiation irradiation source 22A commences, imaging begins. The start of imaging may be determined on the basis of the order from the radiation image processing device 14, the console 16 or the like. Alternatively, as described above, the radiation X is detected at the electronic cassette 20 side, a detected radiation amount is compared with a threshold for irradiation commencement detection, and imaging is considered to start in a case in which the detected radiation amount exceeds the threshold. A timing chart for a case with a low frame rate is shown in FIG. 13, and a timing chart for a case with a high frame rate is shown in FIG. 14. In actual imaging of a radiation image, the TFTs 98 are turned OFF and, after an integration period in which the charges generated by the irradiation of the radiation X are accumulated at the storage capacitors 96, there is a reading period in which the charges accumulated at the storage capacitors 96 are read out. In FIG. 13 and FIG. 14, the integration period is not shown in the drawings; only the reading period is shown.

In step S118, charges are read out from the storage capacitors 96 of the pixels 100 in accordance with the ON and OFF timings of the TFTs 98 set by the processing described above. Then, in step S120, the charges that have been read out and the feedthrough components are integrated at the capacitors C of the amplification circuits 140 over the integration period set by the processing described above.

More specifically, gate signals for turning the gates of the TFTs 98 ON are outputted from the gate line driver 132 to the gate lines 136 sequentially, starting from a first row, at the set timings. When the gates of the TFTs 98 are turned ON, charges are read out from the storage capacitors 96 of the pixels 100 and the charges are outputted to the signal lines 138, and electronic signals flow along the signal lines 138. During the set integration periods, the charges outputted to the signal lines 138 are sampled by the amplifiers 142 of the amplification circuits 140 and the charges are integrated at the capacitors C. In the present exemplary embodiment, control of the integration periods is implemented by turning the switches for charge resetting SW1 of the amplification circuits 140 ON and OFF.

As shown in FIG. 13, in the case with a low frame rate, whereas the driving waveform overlap number is smaller than in the case with a high frame rate, the integration period is set to be longer. Therefore, in the case with the low frame rate, there is some leeway in the integration period, and the generation period t and the generation period t2 may be encompassed within the integration period even if the generation period t1 and generation period t2 do not strictly overlap. Further, the overlap period T of the ON states of the TFTs 98 (for example, in FIG. 13, the overlap period T between the ON state of the TFTs 98 of the gate line 136 in row n−1 and the ON state of the TFTs 98 of the gate line 136 in row n+1) may be made relatively long (at least, compared to a case with a high frame rate). In the present exemplary embodiment, because the generation period t1 and the generation period t2 may be encompassed within the integration period in this case in which there is leeway in the integration period, the ON and OFF timings of the TFTs 98 may be controlled without consideration of the amplitudes and time constants of the feedthrough components.

In contrast, in a case with a high frame rate as shown in FIG. 14, the reset period is shorter and the driving waveform overlap number is greater. Moreover, the integration period is set to be shorter (at least, shorter than in a case with a low frame rate). Consequently, there is no leeway in the integration period and, if the generation period t1 and the generation period t2 are not more strictly overlapped than in the case with a low frame rate, it may not be possible to encompass the generation period t1 and the generation period t2 within the integration period. Therefore, in the case with a high frame rate, the overlap period T of the ON states of the TFTs 98 is made shorter than in a case with a low frame rate. In the present exemplary embodiment, in this case in which there is no leeway in the integration period, the ON and OFF timings of the TFTs 98 are controlled on the basis of a more correct generation period t1 and generation period t2, taking account of the amplitudes and time constants of the feedthrough components, such that the generation period t1 and generation period t2 are encompassed to a significant extent and the feedthrough components may better cancel out.

Even though the driving waveforms of the TFTs 98 are plurally overlapped as illustrated in FIG. 13 and FIG. 14, charges (signal components) from the storage capacitors 96 of the pixels 100 are completely read out in each integration period before the driving waveforms overlap. Therefore, there is no concern about signal components from different pixels 100 mixing together.

In step S122, a determination is made as to whether imaging is ending. In a case in which imaging of all frames has not yet finished, the result of the determination is negative, and the CPU returns to step S118 and repeats the present processing. On the other hand, in a case in which imaging of all frames has finished, or in a case in which imaging of an instructed series of images has finished or the like, the result of the determination is affirmative and the present processing ends.

In the control processing show by the flowchart of FIG. 12, on/off control of the TFTs 98 is implemented with consideration for the amplitudes and time constants of feedthrough components in accordance with the frame rate, but this is not limiting. An alternative example of the control processing is described below.

Figure 15:
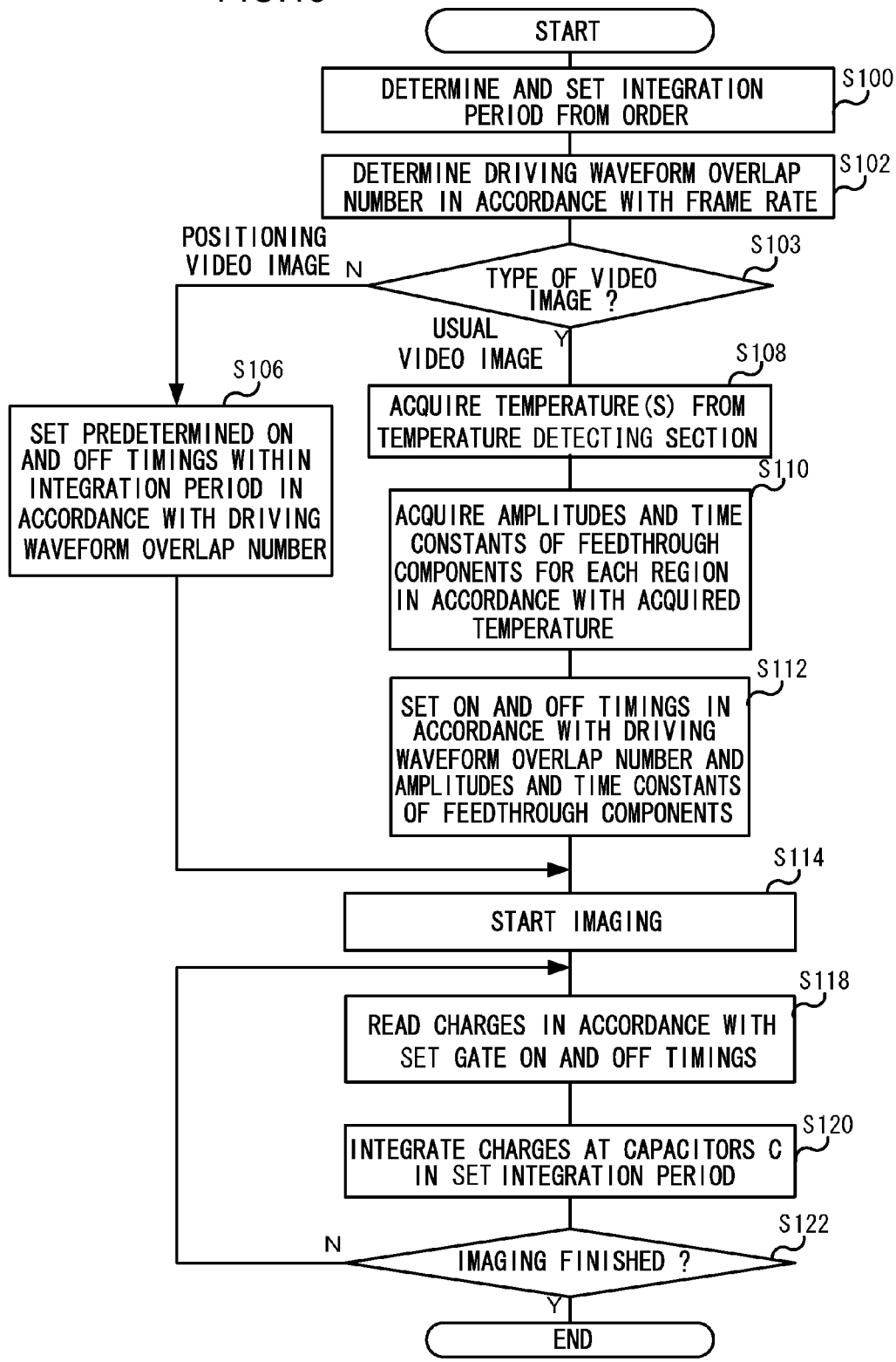
FIG. 15 is a flowchart of an alternative example of the control processing in accordance with the first exemplary embodiment.

Firstly, a case in which ON/OFF control of the TFTs 98 is implemented with consideration for the amplitudes and time constants of the feedthrough components in accordance with a type of video image being imaged rather than the frame rate is described. FIG. 15 shows an example of a flowchart of this control processing. In FIG. 15, steps that are substantially the same as in the control processing shown in FIG. 12 are assigned the same step numbers and are not described; processing that is different is described.

After the integration period is set in step S102, the control processing shown in FIG. 15 is provided with a step S103 instead of step S104 of the control processing shown in FIG. 11.

In some cases, a fluoroscopic image taken during positioning for imaging of a radiation image to be used in diagnostics or the like, positioning for adjusting imaging timings, or the like (hereinafter referred to as a positioning video image) may have a lower image quality than a usual radiation image to be used for diagnostics or checking of a region of interest or the like (hereinafter referred to as a usual video image). In cases of positioning video images, there are many cases in which a higher image quality than a usual video image is not required, and there are cases in which it is acceptable for the feedthrough component to be retained to some extent. Accordingly, in the control processing shown in FIG. 15, the type of a video image is determined in step S103.

In a case of a positioning video image, the CPU proceeds to step S106, and the ON and OFF timings of the TFTs 98 are set in the same manner as in step S106 of FIG. 12 described above. On the other hand, in a case of a usual video image, because higher image quality is required than in a positioning video image, control is applied such that the feedthrough components are cancel out. Therefore, in a case in which it is determined in step S103 that the image is a usual video image, processing the same as that from step S108 onward in FIG. 12 is carried out.

Figure 16:
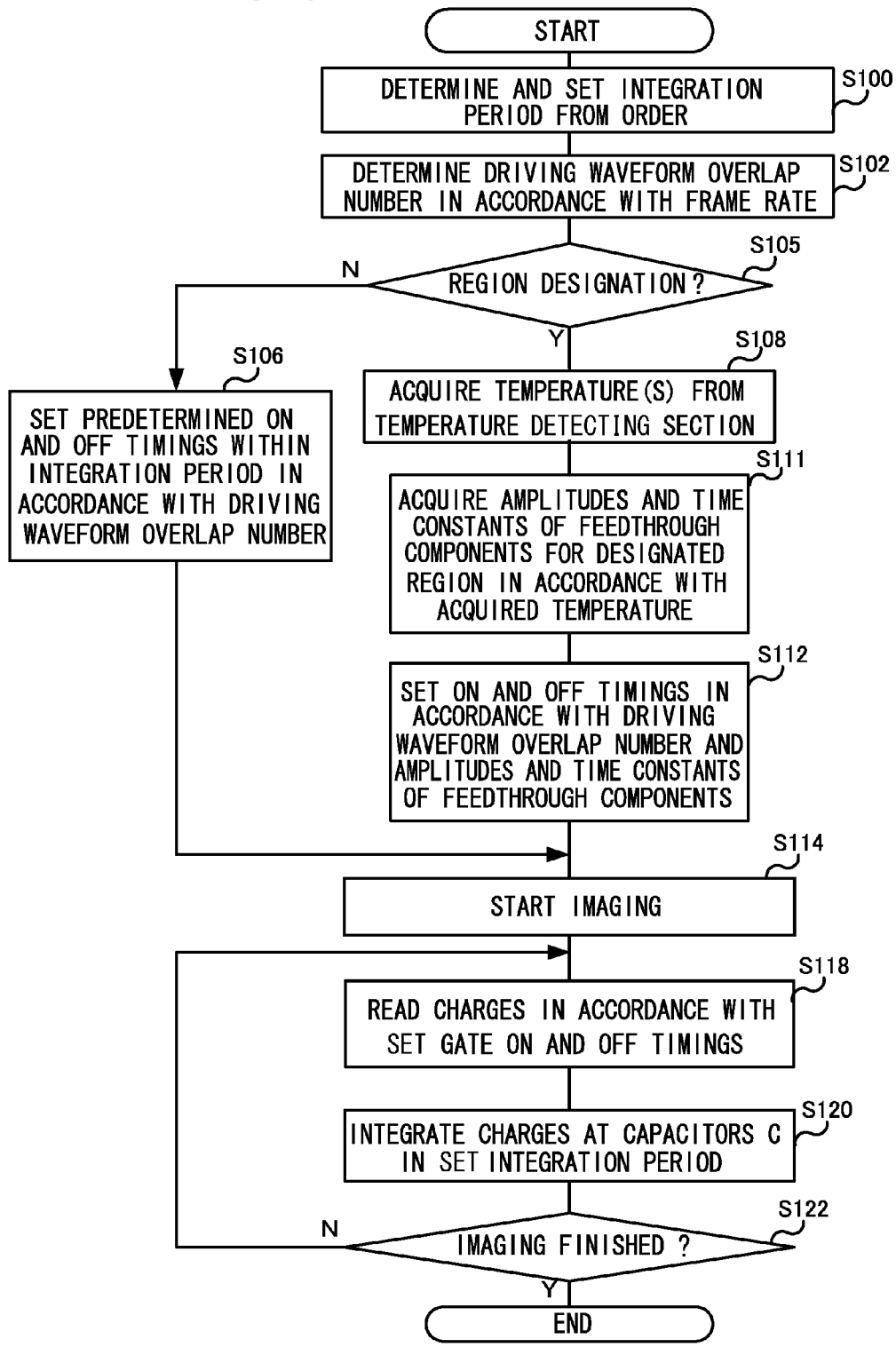
FIG. 16 is a flowchart of another alternative example of the control processing in accordance with the first exemplary embodiment.

Now, a case of implementing ON/OFF control of the TFTs 98 with consideration for the amplitudes and time constants of the feedthrough components in a case in which a region is designated, rather than the frame rate, is described. FIG. 16 shows an example of a flowchart of this control processing. In FIG. 16, steps that are substantially the same as in the control processing shown in FIG. 12 are assigned the same step numbers and are not described; processing that is different is described.

After the integration period is set in step S102, the control processing shown in FIG. 16 is provided with a step S105 instead of step S104 of the control processing shown in FIG. 12.

In the present control processing, rather than control being implemented in accordance with the amplitudes and time constants of the feedthrough components in each region, in a case in which a region is designated, control is implemented in accordance with the amplitudes and time constants of the feedthrough components only in the designated region. For example, for a region other than a region of interest, there are many cases in which a higher image quality than in the region of interest is not required, and there are cases in which it is acceptable for the feedthrough component to be retained to some extent. Accordingly, in step S105 of the control processing shown in FIG. 16, a determination is made as to whether there is a designation of a region. A designation of a region may be an instruction from a user that is received via the communication control section 156, and in a case in which a designation of a region is included in an order, the designation may be acquired from the order.

In a case in which there is no designation of a region, the result of the determination is negative, the CPU proceeds to step S106, and the ON and OFF timings of the TFTs 98 are set in the same manner as in step S106 of FIG. 12 described above. On the other hand, in a case in which there is a designation of a region, because higher image quality is sought for the designated region, control is applied such that the feedthrough components better cancel out. Therefore, in a case in which it is determined in step S103 that the image is a usual video image, the CPU proceeds to step S108 and acquires a temperature from the temperature detecting section 154. Then, in step S111 (which corresponds to step S110 in FIG. 12), the amplitudes and time constants of the feedthrough components in the designated region are acquired in accordance with the acquired temperature. Thereafter, control processing similar to the control processing shown in FIG. 12 is carried out.

Thus, in a case in which there is a designation of a region, the load of the control processing is moderated by implementing ON/OFF control of the TFTs 98 only for the designated region.

In the electronic cassette 20 according to the present exemplary embodiment as described hereabove, the driving waveforms of the TFTs 98 are plurally overlapped, and each integration period of the capacitors C of the amplification circuits 140 is set so as to encompass a feedthrough component (OFF) generation period t2, a feedthrough component (ON) generation period t1, and a period in which charges (the signal component) are read out from the storage capacitors 96 of the pixels 100 by the ON states of the TFTs 98. The number of driving waveforms that are caused to overlap is established in accordance with the frame rate, integration period and reset period, or the like. In a case with a high frame rate, a case of imaging a usual video image or a case of receiving a designation of a region, the temperature of the radiation detector 26 is acquired, and the amplitudes and time constants of feedthrough components that correspond to the temperature are acquired from the table memorized in the memory section 150. In the electronic cassette 20, the ON and OFF timings of the TFTs 98 are controlled in accordance with the acquired amplitudes and time constants of the feedthrough components.

Thus, in the electronic cassette 20 according to the present exemplary embodiment, the driving waveforms of the TFTs 98 are plurally overlapped and the feedthrough component (ON) within an integration period may be cancelled out by a feedthrough component (OFF). Therefore, the feedthrough components may be suppressed. Further, with the electronic cassette 20, a frame rate in imaging of a video image may be raised.

Second Exemplary Embodiment

The present exemplary embodiment includes configurations and operations that are the same as in the first exemplary embodiment described above. Accordingly, configurations and operations that are the same are denoted in the same manner and are not described in detail.

The radiation imaging system 10, the radiation generation device 12, the radiation image processing device 14, the radiation image interpretation device 18, the radiation detector 26, the electronic cassette 20 and the signal processing section 134 are the same as in the first exemplary embodiment, so are not described in detail (see FIG. 1 to FIG. 5).

Figure 19:
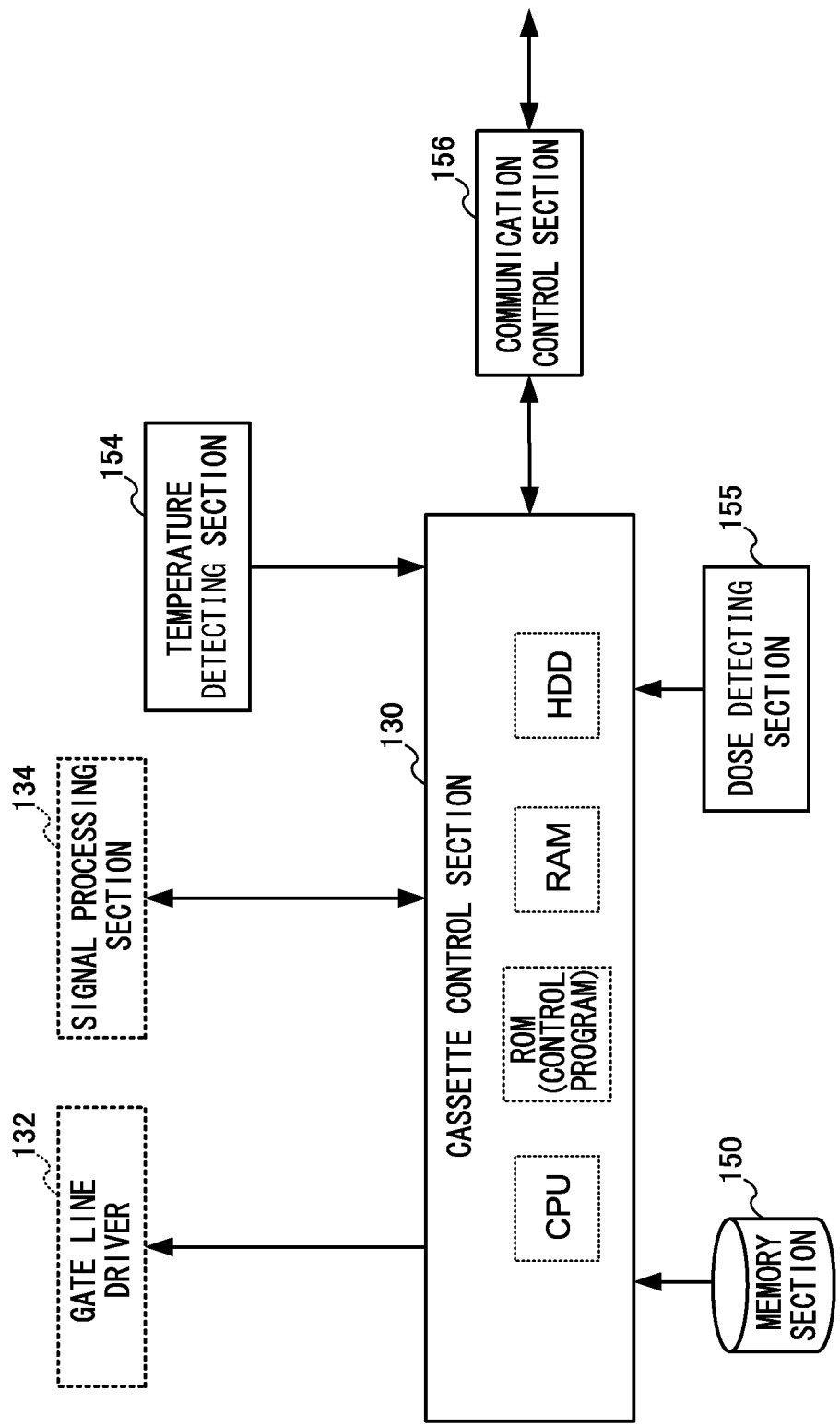
FIG. 19 is a functional block diagram of an example of configurations that correspond to the functions of a cassette control section in an electronic cassette in accordance with a second exemplary embodiment.

In the present exemplary embodiment, some of the functionality of the electronic cassette 20 differs from the first exemplary embodiment. FIG. 19 shows a functional block diagram of an example of configurations corresponding to the functions of the cassette control section 130 of the electronic cassette 20 in accordance with the present exemplary embodiment.

The cassette control section 130 includes functions for controlling overall operations of the electronic cassette 20. The cassette control section 130 according to the present exemplary embodiment also has a function for, in a case in which a radiation image is being imaged, controlling periods of integration of charges at the capacitors C of the amplification circuits 140 and timings at which the gates of the TFTs 98 are turned ON and OFF (described in detail herebelow).

The cassette control section 130 is provided with a CPU, ROM, RAM and an HDD. The CPU includes functions for controlling overall operations of the electronic cassette 20. Various programs including a control program to be used at the CPU and suchlike are pre-memorized in the ROM. The RAM includes functions for temporarily storing various kinds of data. The HDD includes functions for storing and retaining various kinds of data.

The communication control section 156 includes functions for exchanging various kinds of information, including image information of radiation images, with the radiation image processing device 14, the console 16 and suchlike by wireless communications and wired communications.

The temperature detecting section 154 has a function for detecting a temperature of the electronic cassette 20, more preferably a temperature of the radiation detector 26. The temperature detected by the temperature detecting section 154 is outputted to the cassette control section 130. The temperature detecting section 154 may be plurally provided at the radiation detector 26.

The dose detecting section 155 has a function for detecting a dose of the radiation X that is irradiated on the electronic cassette 20. The configuration of the dose detecting section 155 is not particularly limited; it is sufficient if the dose detecting section 155 can sense the radiation X irradiated on the electronic cassette 20 through a predetermined detecting period and compare the dose irradiated during the detecting period with a predetermined threshold, a profile or the like. The configuration of the dose detecting section 155 may be, for example, a configuration that is provided in the radiation detector 26 for detecting the radiation X, and some of the pixels 100 may be used as pixels for detecting. Pixels 100 in which the TFTs 98 are short-circuited or the like may be used as these pixels for detecting, but this is not a limitation. Further, a sensor that detects the dose may be provided separately. Further yet, in a case in which automatic exposure control (AEC) processing is applied at the electronic cassette 20 side during imaging to control operations for imaging of a radiation image, an AEC processing configuration may be used. The term "dose" as used in the present exemplary embodiment is intended to include a "mAs" value in which a tube current (mA) in a case in which the radiation X is being produced is multiplied by an irradiation duration (s).

The cassette control section 130 controls the radiation detector 26 so as to carry out imaging of a radiation image in accordance with an imaging menu selection that includes imaging conditions and the like, for in a case in which a radiation image is being imaged, which are received by the communication control section 156.

The cassette control section 130 performs control to set the integration periods of the capacitors C of the amplification circuits 140 and the ON and OFF timings of the TFTs 98, taking account of the frame rate, the type of video image and the like, and, on the basis of temperatures detected by the temperature detecting section 154 and the like, the amplitudes and time constants of feedthrough components. In order to simplify the descriptions herebelow, a feedthrough component that is generated by the TFTs 98 connected to a given gate line 136 being turned OFF is referred to as "the feedthrough component (OFF)", and a feedthrough component that is generated by the TFTs 98 connected to a subsequent gate line 136 after the given gate line 136 being turned ON is referred to as "the feedthrough component (ON)".

In the present exemplary embodiment, the integration period of the capacitors C is set so as to encompass an integration period in which the feedthrough component (OFF) is integrated, and an integration period in which the feedthrough component (ON) and the charges read out from the storage capacitors 96 of the pixels 100 in accordance with the ON state are integrated. The cassette control section 130 controls the ON and OFF timings of the TFTs 98 in accordance with the set integration periods.

The feedthrough component in the present exemplary embodiment is the same as in the first exemplary embodiment, as described herebelow. In a case in which numerous switching elements such as the TFTs 98 or the like are arranged in a two-dimensional pattern, as in the TFT active matrix substrate used in the radiation detector 26 according to the present exemplary embodiment, the plural gate lines for turning the switching elements ON and OFF and the plural signal lines for transferring the electronic signals from the pixels whose switching elements have been turned ON form an intersecting arrangement. Thus, parasitic capacitances occur. In the radiation detector 26, in a case in which a switching element is turned ON or is turned OFF, the amplitude of a voltage applied to the parasitic capacitance at the point of intersection between the gate line and the signal line that are connected to that switching element is changed. Consequently, induced charges are produced on the parasitic capacitance. The induced charges arising at the parasitic capacitance are superimposed on the charges being transferred through the signal line (signal charges for a radiation image) in the form of a noise component which is a signal (charges) referred to as a feedthrough component.

FIG. 7, presented in the first exemplary embodiment, shows the relationship between ON/OFF control of a switching element and the generated feedthrough components. Energy amounts (charge amounts) of the feedthrough component (ON) and the feedthrough component (OFF) are the same, but the feedthrough components differ between positive and negative, and differ in profile. As illustrated in FIG. 7, it is characteristic that the generation period t2 of the feedthrough component (OFF) is longer than the generation period t1 of the feedthrough component (ON). The generation periods t1 and t2 of the feedthrough components (ON) and (OFF) differ depending on amplitudes and time constants of the feedthrough components.

The amplitudes of the generated feedthrough components differ in accordance with the position of the TFT 98 in the radiation detector 26. In general, the longer the lengths of the gate lines 136 and the signal lines 138, the larger the feedthrough components. Specifically, in the present exemplary embodiment, the longer a sum of the length of the gate line 136 from the gate line driver 132 to the TFT 98 of a pixel 100 and the length of the signal line 138 from the signal processing section 134 to the TFT 98 of the pixel 100, the larger the feedthrough components. Accordingly, in the present exemplary embodiment, an area (region) of the radiation detector 26 on which the radiation X is irradiated is divided into a plural number of regions, and control is applied in accordance with the amplitudes of the feedthrough components in the respective divided regions. FIG. 8A and FIG. 8B, presented in the first exemplary embodiment, show specific examples of these regions. FIG. 8A shows a case of division into six regions (blocks A, A', B, B', C and C'). In the case shown in FIG. 8A, the feedthrough component is largest in block A', which is furthest from the gate line driver 132 and the signal processing section 134, and the feedthrough component is smallest in block C, which is closest to the gate line driver 132 and the signal processing section 134, in the case shown in FIG. 8A.

In a case of division such that there are plural regions in the row direction, for example, the case shown in FIG. 8A, it is desirable, as in the electronic cassette 20 in FIG. 9, presented in the first exemplary embodiment, to provide the gate line driver 132 to output gate signals to block A, block B and block C, and the gate line driver 132' to output gate signals to block A', block B' and block C'. In FIG. 9, the gate line driver 132 and the gate line driver 132' are configured as separate units, but the same may be configured as a single gate line driver.

FIG. 8B shows a case of division into two regions, a central portion of the area on which the radiation X is irradiated (block A) and an outer edge portion (block B). In general, imaging is performed such that a region of interest of the imaging subject 30 is disposed at a middle portion of the area on which radiation X is irradiated, such that the region of interest is imaged at the middle of the radiation image. Thus, in radiation images, higher image quality is required towards the central portion (block A). Therefore, it is preferable to set the regions in this manner in a case of applying control that distinguishes the central portion from other regions, such that the feedthrough component is controlled more appropriately. Note that methods of dividing up the regions are not limited to the above.

In a case of division into plural regions as shown in FIG. 8A and FIG. 8B, it is preferable to provide the temperature detecting section 154 in each region or in each of predetermined regions, such that the respective temperatures thereof may be detected.

FIG. 10, illustrated in the first exemplary embodiment, shows correspondences between the amplitudes of the feedthrough components and temperature. FIG. 10 illustrates, as an example, correspondences for block A and block B shown in FIG. 8A. The feedthrough components differ with the amplitudes of the voltages applied to the gates when the TFTs 98 are turned ON and OFF. Accordingly, in this case the amplitudes of the feedthrough components are shown for 20 V, which is a gate voltage that is ordinarily applied in the present exemplary embodiment when reading from the storage capacitors 96 of the pixels 100.

FIG. 11, illustrated in the first embodiment, shows a correspondence between the time constants of the feedthrough components and temperature. In general, leakage currents in the TFTs 98 increase in a case in which the temperature of the radiation detector 26 is higher. Therefore, as shown in FIG. 11, the higher the temperature of the radiation detector 26, the smaller the time constants of the feedthrough components; and the smaller the time constants, the shorter the generation periods t and t2 as shown in FIG. 7.

In the present exemplary embodiment, a table representing the correspondences shown in FIG. 10 and FIG. 11 for each region (block) is memorized in the memory section 150 in advance. The amplitudes of the feedthrough components and the table may be prepared in advance on the basis of offset images (images that are imaged in a state in which the radiation X is not being irradiated) that are acquired with the ON and OFF timings of the TFTs 98 being arbitrarily set. For the amplitudes of the feedthrough components used in the table, an average value or a maximum value or the like of the TFTs 98 of the pixels 100 in each region (block) may be used. Which value is used is not particularly limited, and may differ between the regions.

In the electronic cassette 20 according to the present exemplary embodiment (the radiation detector 26), the charge amounts accumulated at the storage capacitors 96 of the individual pixels 100 are small; the signal charges being transferred along the signal lines are of the same order as the order of the feedthrough components. Therefore, the effects of the feedthrough components cannot be disregarded. In particular, in a case of video imaging, the dose of each image is smaller than in still imaging. Therefore, the charge amounts accumulated at the storage capacitors 96 of the pixels 100 are small, and the effect of the feedthrough components may be larger. Therefore, in video imaging with small doses of the radiation X, it is necessary to suppress the effects of the feedthrough components.

Specifically, in the present exemplary embodiment, the effects of the feedthrough components may be suppressed by cancelling out a feedthrough component (ON) with a feedthrough component (OFF). Accordingly, in the electronic cassette 20, the integration period of the capacitors C of the amplification circuits 140 is set so as to encompass an integration period in which charges (signals) read out from a pixel 100 are integrated, the feedthrough component (ON) generation period t1 and the feedthrough component (OFF) generation period t2. In the present exemplary embodiment, the generation period t1 is considered to be equal to the integration period for integrating the feedthrough component (ON), and the generation period t2 is considered to be equal to the integration period for integrating the feedthrough component (OFF).

As a consequence of this specification, in a case in which the charges are being integrated at the capacitor C of an amplification circuit 140 in the electronic cassette 20, the feedthrough component (ON) is cancelled out by the feedthrough component (OFF). Therefore, in the electronic cassette 20, the feedthrough components that are superimposed on the charges (signals) read out from the pixels 100 may be suppressed.

In imaging of video images, a higher frame rate is sometimes required. For example, in video imaging in general, 15 fps is said to be adequate for images of the digestive system, 30 fps is considered adequate for images of the circulatory system, and 60 fps is considered adequate for images of children. However, with higher frame rates up to, for example, 120 fps or the like, movements of the heart and the like may be smoothly seen. In particular, a frame rate of the order of 120 fps is preferable for imaging the heart of a child. Moreover, in imaging using a radiocontrast agent, tracing may be possible with a smaller amount of the radiocontrast agent in a case in which the frame rate is higher. Using smaller doses of radiocontrast agents is preferable, because radiocontrast agents may cause side effects.

In general, an upper limit on the integration period of the capacitors C of the amplification circuits 140 is governed by the frame rate. In a case of imaging at a high frame rate, an imaging duration for each frame is shorter than in a case of imaging at a low frame rate, and the integration period of the capacitors C of the amplification circuits 140 is shorter. In a case in which the integration period is longer, there is a higher degree of freedom in control of the ON and OFF timings of the TFTs 98 to encompass the feedthrough component (ON) generation period t1 and the feedthrough component (OFF) generation period t2 in the integration period. For example, even in a case in which the generation period t1 and the generation period t2 do not overlap, the feedthrough component (ON) and the feedthrough component (OFF) may cancel out. That is, even in a case in which a period in which the TFTs 98 connected to the gate line 136 of a given row are turned ON and a period in which the TFTs 98 connected to the gate line 136 of the subsequent row after the given row are turned ON do not overlap, the feedthrough components may be able to cancel out.

On the other hand, in a case in which the integration period is short, there is a lower degree of freedom of control of the ON and OFF timings of the TFTs 98, and the generation period t1 and generation period t2 must overlap to a significant extent. In this case, the ON and OFF timings of the TFTs 98 must be controlled such that, for example, whichever period is longer of the generation period t1 and the generation period t2 may completely encompass the shorter period. That is, an overlap period T, in which the period in which the TFTs 98 connected to the gate line 136 of a given row are turned ON and the period in which the TFTs 98 connected to the gate line 136 of a subsequent row after the given row are turned ON overlap, must be more strictly controlled.

Thus, in consideration of these facts, in order to suppress the feedthrough components in imaging at a high frame rate in the electronic cassette 20 according to the present exemplary embodiment, in a case in which the frame rate is above a predetermined threshold (a high frame rate): a temperature is acquired from the aforementioned temperature detecting section 154; the amplitudes and time constants of of feedthrough components corresponding to the acquired temperature are acquired from the table memorized in the memory section 150; and the ON and OFF timings of the TFTs 98 are controlled accordingly.

The specification of the integration period of the capacitors C of the amplification circuits 140 and control of the ON and OFF timings of the TFTs 98 in the electronic cassette 20 according to the present exemplary embodiment, in accordance with the feedthrough components, are described in detail with reference to the attached drawings.

Figure 20:
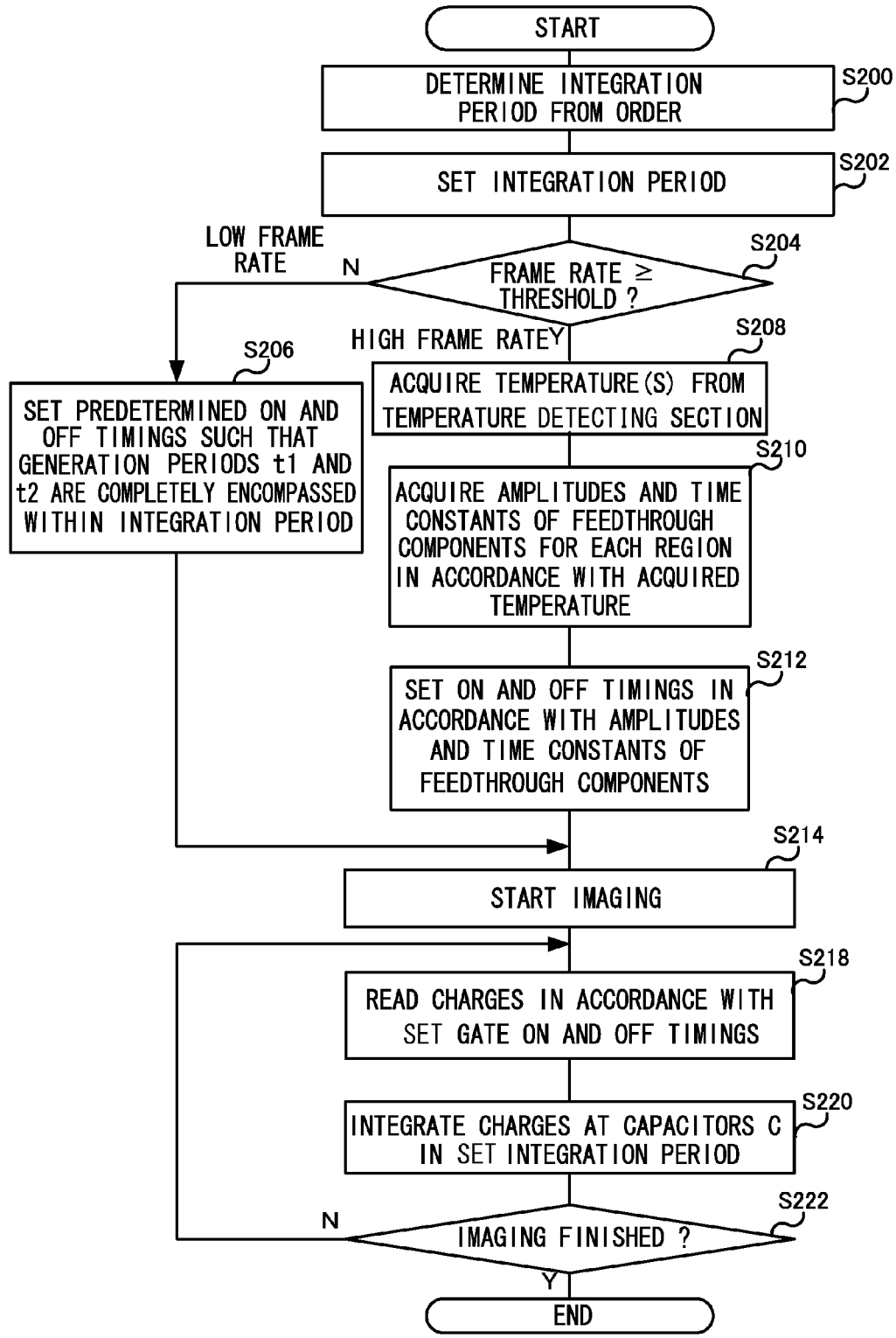
FIG. 20 is a flowchart showing an example of control processing in a case of switching control of ON and OFF timings of a TFT in accordance with a frame rate in the electronic cassette in accordance with the second exemplary embodiment.

First, control processing in a case in which control of the ON and OFF timings of the TFTs 98 is switched in accordance with the frame rate is described. FIG. 20 shows a flowchart of an example of this control processing in the present exemplary embodiment. This control processing of the present exemplary embodiment is carried out by a control processing control program being executed by the CPU of the cassette control section 130. In the present exemplary embodiment, this control program is memorized in advance in the ROM of the cassette control section 130, or the memory section 150 or the like. Configurations are also possible in which the control program is downloaded from an external system (the RIS) or a CD-ROM, or via USB or the like.

The present control processing is executed in a case in which an order representing imaging conditions is received by the communication control section 156 and imaging of a radiation image is commanded. First, in step S200, the integration period of the capacitors C of the amplification circuits 140 is determined from the acquired order. In the present exemplary embodiment, the frame rate is included in the order. In general, an upper limit on the integration period is determined from the frame rate. Specifically, in the present exemplary embodiment, the reading period for one frame, in which the charges accumulated at the storage capacitors 96 of the pixels 100 are read out, is established from the frame rate. The reading period includes an integration period and a reset period for each of the gate lines 136 (including an ADC period of the amplification circuits 140 and a reset period for the integrated charges). Therefore, the integration period is determined from the reading period for one frame, the reset period, the number of the gate lines 136, and the like. In the present exemplary embodiment, there is an upper limit on the integration period, but this is not a limitation and the integration period may be a period shorter than the upper limit. In a case in which the integration period has been determined, in the following step S202, the determined integration period is set as the charge integration period of the capacitors C of the amplification circuits 140.

In step S204, a determination is made as to whether the frame rate is above a threshold. In the present exemplary embodiment, the threshold that defines high frame rates is determined and memorized in the memory section 150 or the like in advance. In this step, in a case in which the result of the comparison with the threshold is negative, the frame rate is a low frame rate, and accordingly the CPU proceeds to step S206.

In step S206, the ON and OFF timings of predetermined TFTs 98 are set such that the generation periods t1 and t2 are completely encompassed within the set integration periods. Then the CPU proceeds to step S214. In the present exemplary embodiment, the ON and OFF timings of the TFTs 98 in this case are determined in advance in accordance with the specifications of the radiation detector 26, image qualities of radiation images and so forth. A timing at which TFTs 98 are turned ON is ordinarily determined in accordance with the frame rate. Therefore, in the present exemplary embodiment, it is the timing at which the TFTs 98 are turned OFF that is adjusted.

On the other hand, in a case in which the result of the determination in step S204 is that the frame rate is above the threshold, this is a high frame rate and accordingly the CPU proceeds to step S208. In step S208, the temperature(s) of the radiation detector 26 is/are acquired from the temperature detecting section 154. A method of acquisition of temperature from the temperature detecting section 154 may be, for example, detecting the temperature of each region with the temperature detecting section 154 and acquiring the temperature for each region from the temperature detecting section 154. Alternatively, the temperature at a predetermined region may be detected by the temperature detecting section 154 and the temperature of each region estimated from the detected temperature. Further, temperature characteristics of the radiation detector 26 may be ascertained in advance, and the temperature of each region estimated on the basis of the temperature characteristics and a temperature detected by the temperature detecting section 154. This acquisition method is not particularly limited, but it is preferable to acquire or estimate a temperature for each region.

In step S210, in accordance with the acquired temperatures, the amplitudes and time constants of the feedthrough components in each region (block) are looked up in the table memorized in the memory section 150 and acquired therefrom.

In step S212, depending on the acquired feedthrough component amplitudes and time constants, the ON and OFF timings of the TFTs 98 are set. In the present exemplary embodiment, relationships between these feedthrough component amplitudes and time constants and the generation periods t1 and t2 are obtained in advance and memorized in the memory section 150. On the basis thereof, the ON and OFF timings of the TFTs 98 and an overlap period T of the ON-periods are set (see FIG. 21 and FIG. 22).

Figure 21:
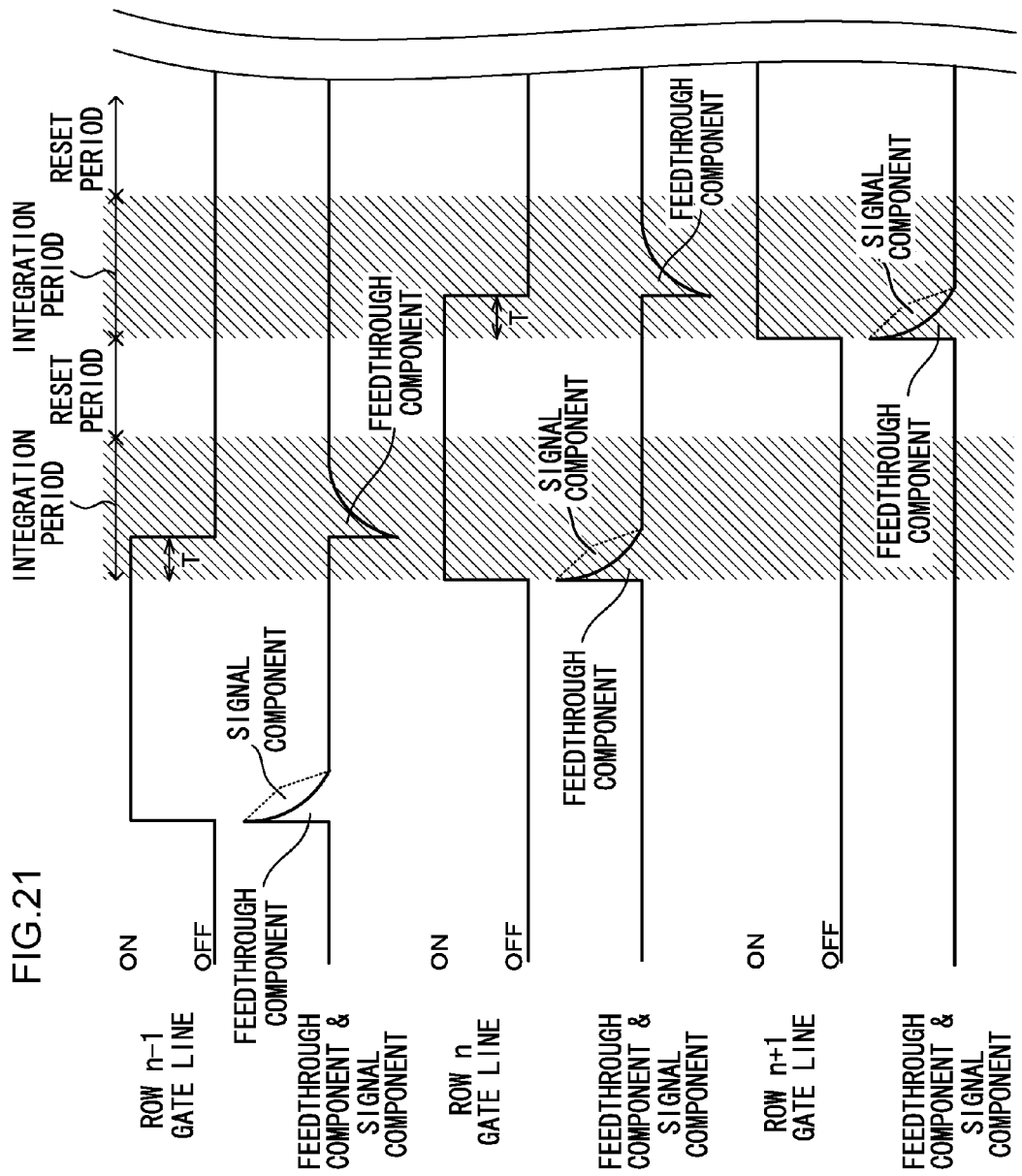
FIG. 21 is a timing chart of an example of a case of imaging at a low frame rate in the control processing of the electronic cassette in accordance with the second exemplary embodiment.
Figure 22:
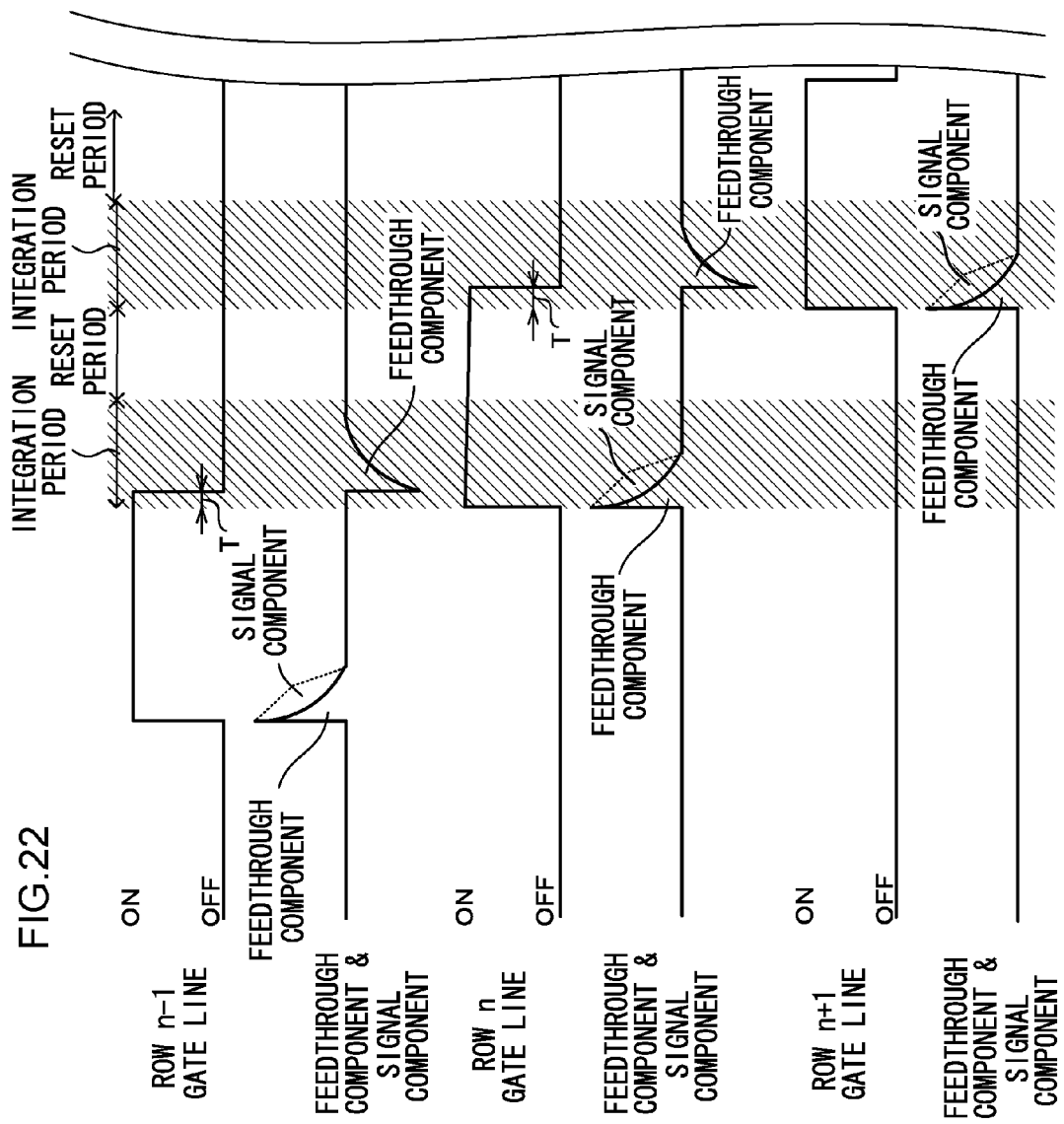
FIG. 22 is a timing chart of an example of a case of imaging at a high frame rate in the control processing of the electronic cassette in accordance with the second exemplary embodiment.

In step S214, in a case in which an irradiation of the radiation X from the radiation irradiation source 22A commences, imaging begins. The start of imaging may be determined on the basis of a command from the radiation image processing device 14, the console 16 or the like. Alternatively, as described above, the radiation X is detected at the electronic cassette 20 side, a detected radiation amount is compared with a threshold for irradiation commencement detection, and imaging is considered to start in a case in which the detected radiation amount exceeds the threshold. A timing chart for a case with a low frame rate is shown in FIG. 21, and a timing chart for a case with a high frame rate is shown in FIG. 22. In actual imaging of a radiation image, the TFTs 98 are turned OFF and, after an integration period in which the charges generated by the irradiation of the radiation X are accumulated at the storage capacitors 96, there is a reading period in which the charges accumulated at the storage capacitors 96 are read out. In FIG. 21 and FIG. 22, the integration period is not shown in the drawings; only the reading period is shown.

In step S218, charges are read out from the storage capacitors 96 of the pixels 100 in accordance with the ON and OFF timings of the TFTs 98 set by the processing described above. Then, in step S220, the charges that have been read out and the feedthrough components are integrated at the capacitors C of the amplification circuits 140 over the integration period set by the processing described above.

More specifically, gate signals for turning the gates of the TFTs 98 ON are outputted from the gate line driver 132 to the gate lines 136 sequentially, starting from a first row, at the set timings. In a case in which the gates of the TFTs 98 are turned ON, charges are read out from the storage capacitors 96 of the pixels 100 and the charges are outputted to the signal lines 138, and electronic signals flow along the signal lines 138. During the set integration periods, the charges outputted to the signal lines 138 are sampled by the amplifiers 142 of the amplification circuits 140 and the charges are integrated at the capacitors C. In the present exemplary embodiment, control of the integration periods is implemented by turning the switches for charge resetting SW1 of the amplification circuits 140 ON and OFF.

As shown in FIG. 21, in the case with a low frame rate, the integration period is set to be longer (at least, longer than in a case with a high frame rate). Therefore, in the case with the low frame rate, there is some leeway in the integration period, and the generation period t1 and the generation period t2 may be encompassed within the integration period even if the generation period t1 and generation period t2 do not strictly overlap. Further, the overlap period T of the ON states of the TFTs 98 (for example, in FIG. 21, the overlap period T between the ON state of the TFTs 98 of the gate line 136 in row n−1 and the ON state of the TFTs 98 of the gate line 136 in row n) may be made relatively long (at least, compared to a case with a high frame rate). In the present exemplary embodiment, because the generation period t1 and the generation period t2 may be encompassed within the integration period in this case in which there is leeway in the integration period, the ON and OFF timings of the TFTs 98 may be controlled without consideration of the amplitudes and time constants of the feedthrough components.

On the other hand, in a case with a high frame rate as shown in FIG. 22, the integration period is set to be shorter (at least, shorter than in a case with a low frame rate). Consequently, in a case with a high frame rate, there is no leeway in the integration period and, if the generation period t1 and the generation period t2 are not more strictly overlapped than in the case with a low frame rate, it may not be possible to encompass the generation period t1 and the generation period t2 within the integration period. Therefore, the overlap period T of the ON states of the TFTs 98 is made shorter than in a case with a low frame rate.

In the present exemplary embodiment, in this case in which there is no leeway in the integration period, the ON and OFF timings of the TFTs 98 are controlled on the basis of a more correct generation period t1 and generation period t2, taking account of the amplitudes and time constants of the feedthrough components, such that the generation period t1 and generation period t2 are encompassed to a significant extent and the feedthrough components may better cancel out.

In step S222, a determination is made as to whether imaging is ending. In a case in which imaging of all frames has not yet finished, the result of the determination is negative, and the CPU returns to step S218 and repeats the present processing. On the other hand, in a case in which imaging of all frames has finished, or in a case in which imaging of an instructed series of images has finished or the like, the result of the determination is affirmative and the present processing ends.

In the control processing show by the flowchart of FIG. 20, ON/OFF control of the TFTs 98 is implemented with consideration for the amplitudes and time constants of feedthrough components in accordance with the frame rate, but this is not limiting. An alternative example of the control processing is described below.

Figure 23:
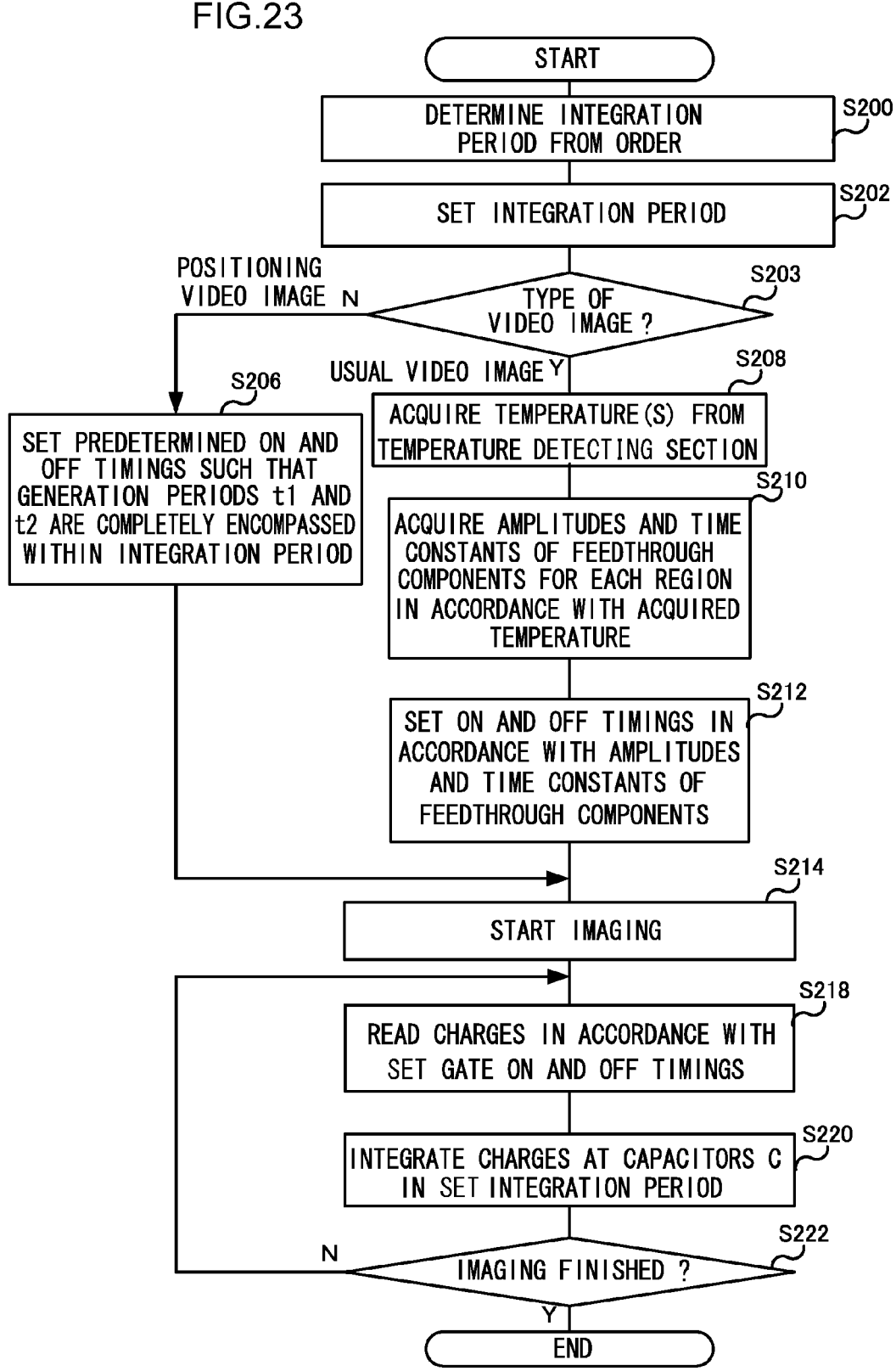
FIG. 23 is a flowchart of an alternative example of the control processing in accordance with the second exemplary embodiment.

Firstly, a case in which ON/OFF control of the TFTs 98 is implemented with consideration for the amplitudes and time constants of the feedthrough components in accordance with a type of video image being imaged rather than the frame rate is described. FIG. 23 shows an example of a flowchart of this control processing. In FIG. 23, steps that are substantially the same as in the control processing shown in FIG. 20 are assigned the same step numbers and are not described; processing that is different is described.

After the integration period is set in step S202, the control processing shown in FIG. 23 is provided with a step S203 instead of step S204 of the control processing shown in FIG. 20.

In some cases, a fluoroscopic image taken during positioning for imaging of a radiation image to be used in diagnostics or the like, positioning for adjusting imaging timings, or the like (hereinafter referred to as a positioning video image) may have a lower image quality than a usual radiation image to be used for diagnostics or checking of a region of interest or the like (hereinafter referred to as a usual video image). In cases of positioning video images, there are many cases in which a higher image quality than a usual video image is not required, and there are cases in which it is acceptable for the feedthrough component to be retained to some extent. Accordingly, in the control processing shown in FIG. 23, the type of a video image is determined in step S203.

In a case of a positioning video image, the CPU proceeds to step S206, and the ON and OFF timings of the TFTs 98 are set in the same manner as in step S206 of FIG. 20 described above. On the other hand, in a case of a usual video image, because higher image quality is sought than in a positioning video image, control is applied such that the feedthrough components better cancel out. Therefore, in a case in which it is determined in step S203 that the image is a usual video image, processing the same as that from step S208 onward in FIG. 20 is carried out.

Figure 24:
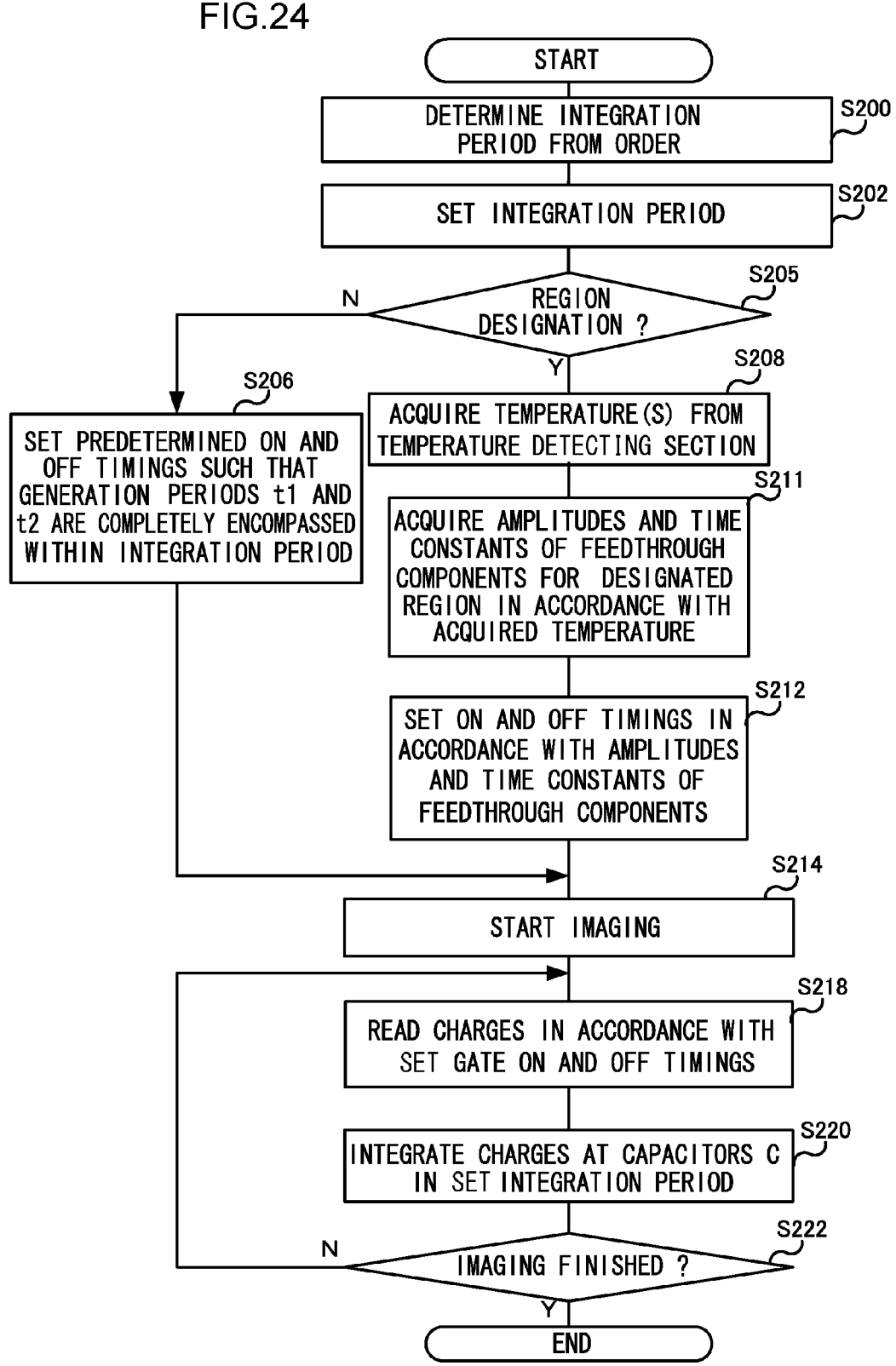
FIG. 24 is a flowchart of another alternative example of the control processing in accordance with the second exemplary embodiment.

Now, a case of implementing ON/OFF control of the TFTs 98 with consideration for the amplitudes and time constants of the feedthrough components in a case in which a region is designated, rather than the frame rate, is described. FIG. 24 shows an example of a flowchart of this control processing. In FIG. 24, steps that are substantially the same as in the control processing shown in FIG. 20 are assigned the same step numbers and are not described; processing that is different is described.

After the integration period is set in step S202, the control processing shown in FIG. 24 is provided with a step S205 instead of step S204 of the control processing shown in FIG. 20.

In the present control processing, rather than control being implemented in accordance with the amplitudes and time constants of the feedthrough components in each region, in a case in which a region is designated, control is implemented in accordance with the amplitudes and time constants of the feedthrough components only in the designated region. For example, for a region other than a region of interest, there are many cases in which a higher image quality than in the region of interest is not required, and there are cases in which it is acceptable for the feedthrough component to be retained to some extent. Accordingly, in step S205 of the control processing shown in FIG. 23, a determination is made as to whether there is a designation of a region. A designation of a region may be an instruction from a user that is received via the communication control section 156, and in a case in which a designation of a region is included in an order, the designation may be acquired from the order.

In a case in which there is no designation of a region, the result of the determination is negative, the CPU proceeds to step S206, and the ON and OFF timings of the TFTs 98 are set in the same manner as in step S206 of FIG. 20 described above. On the other hand, in a case in which there is a designation of a region, because higher image quality is sought for the designated region, control is applied such that the feedthrough components better cancel out. Therefore, in a case in which it is determined in step S203 that the image is a usual video image, the CPU proceeds to step S208 and acquires a temperature from the temperature detecting section 154. Then, in step S211 (which corresponds to step S210 in FIG. 20), the amplitudes and time constants of the feedthrough components in the designated region are acquired in accordance with the acquired temperature. Thereafter, control processing similar to the control processing shown in FIG. 20 is carried out.

Thus, in a case in which there is a designation of a region, the load of the control processing is moderated by implementing ON/OFF control of the TFTs 98 only for the designated region.

In the electronic cassette 20 according to the present exemplary embodiment as described hereabove, each integration period of the capacitors C of the amplification circuits 140 is set so as to encompass a feedthrough component (OFF) generation period t2, a feedthrough component (ON) generation period t1, and a period in which charges (the signal component) are read out from the storage capacitors 96 of the pixels 100 by the ON states of the TFTs 98. In a case with a high frame rate, a case of imaging a usual video image or a case of receiving a region designation, the temperature of the radiation detector 26 is acquired, and the amplitudes and time constants of feedthrough components that correspond to the temperature are acquired from the table memorized in the memory section 150. In the electronic cassette 20, the ON and OFF timings of the TFTs 98 are controlled in accordance with the acquired amplitudes and time constants of the feedthrough components.

Thus, in the electronic cassette 20 according to the present exemplary embodiment, the feedthrough component (ON) within an integration period may be cancelled out by a feedthrough component (OFF). Therefore, the feedthrough components may be suppressed. Further, with the electronic cassette 20, a frame rate in imaging of a video image may be raised.

Now, as is shown in FIG. 13, FIG. 14, FIG. 17 and FIG. 18 for the first exemplary embodiment and FIG. 21, FIG. 22, FIG. 25 and FIG. 26 for the second exemplary embodiment, there is no feedthrough component (OFF) signal to cancel out the feedthrough component (ON) for the TFTs 98 that are turned ON first in the radiation detector 26. In this case, charges that are read out from the pixels 100 corresponding to the gate line 136 through which signals for applying the gate voltage first flow may be discarded (not used for radiation images). Similarly, for the TFTs 98 that are turned ON last, there is no feedthrough component (ON) to be cancelled out by the feedthrough component (OFF) thereof. Accordingly, the same measure as described above may be applied. The above is not limiting; a gate line 136 for generating a cancelling feedthrough component may be separately provided. The same signals as in the usual gate lines 136 may flow in this gate line 136 to generate a feedthrough component, and the generated feedthrough component may be used for cancelling out.

The overlap number of the driving waveforms of the TFTs 98 is not limited by the above descriptions. For example, the overlap number of the driving waveforms of the TFTs 98 may be varied in accordance with the type of video image and the like.

Figure 17:
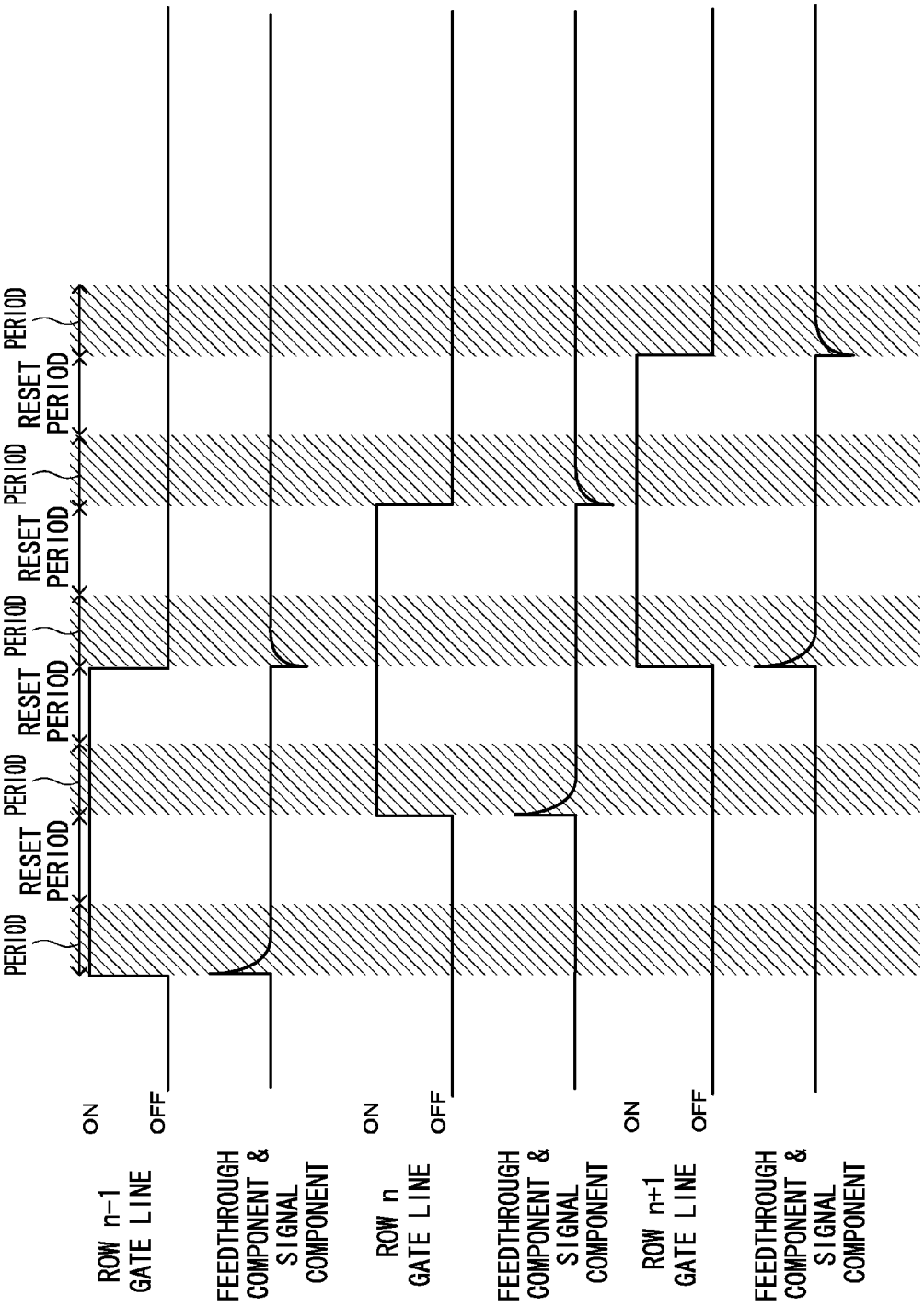
FIG. 17 is a timing chart of an alternative example of the control processing of the electronic cassette in accordance with the first exemplary embodiment.
Figure 25:
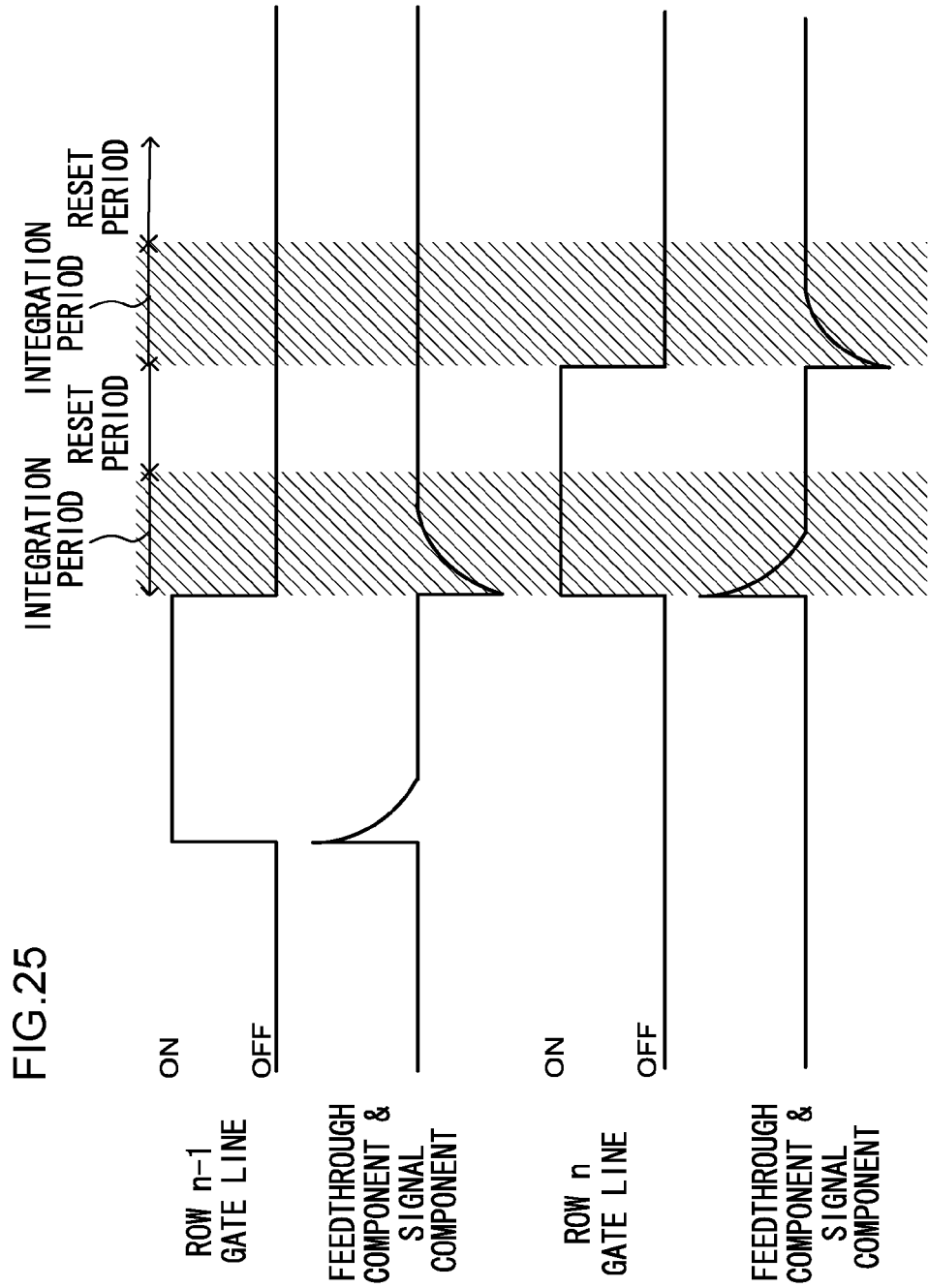
FIG. 25 is a timing chart of an alternative example of the control processing of the electronic cassette in accordance with the second exemplary embodiment.

In the first exemplary embodiment and second exemplary embodiment described above, as shown in FIG. 13, FIG. 14, FIG. 21 and FIG. 22, the ON and OFF timings of the TFTs 98 are controlled so as to encompass the overlap period T, but this is not a limitation. For example, in the electronic cassette 20, as shown in FIG. 17 and FIG. 25, the timings may be controlled such that the overlap period T is zero and the TFTs 98 are considered to turn ON and OFF simultaneously. In this case, the feedthrough components may cancel out more correctly. Because the feedthrough components may cancel one another out directly in a case in which the overlap period T is shorter, the gain of the amplifiers 142 of the amplification circuits 140 may be raised, which is preferable. Furthermore, the feedthrough components may cancel out more correctly in a case in which the generation period t1 and the generation period t2 overlap at least partially, and therefore overlapping is preferable.

Figure 18:
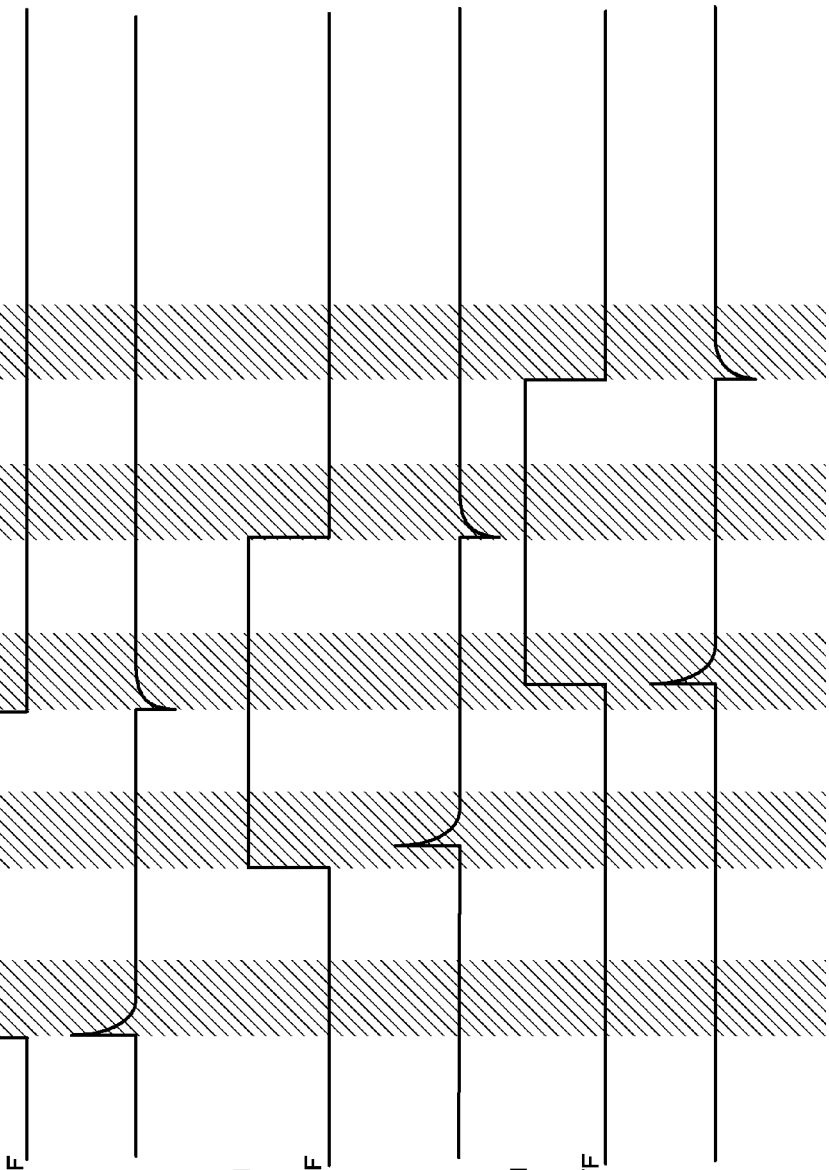
FIG. 18 is a timing chart of another alternative example of the control processing of the electronic cassette in accordance with the first exemplary embodiment.
Figure 26:
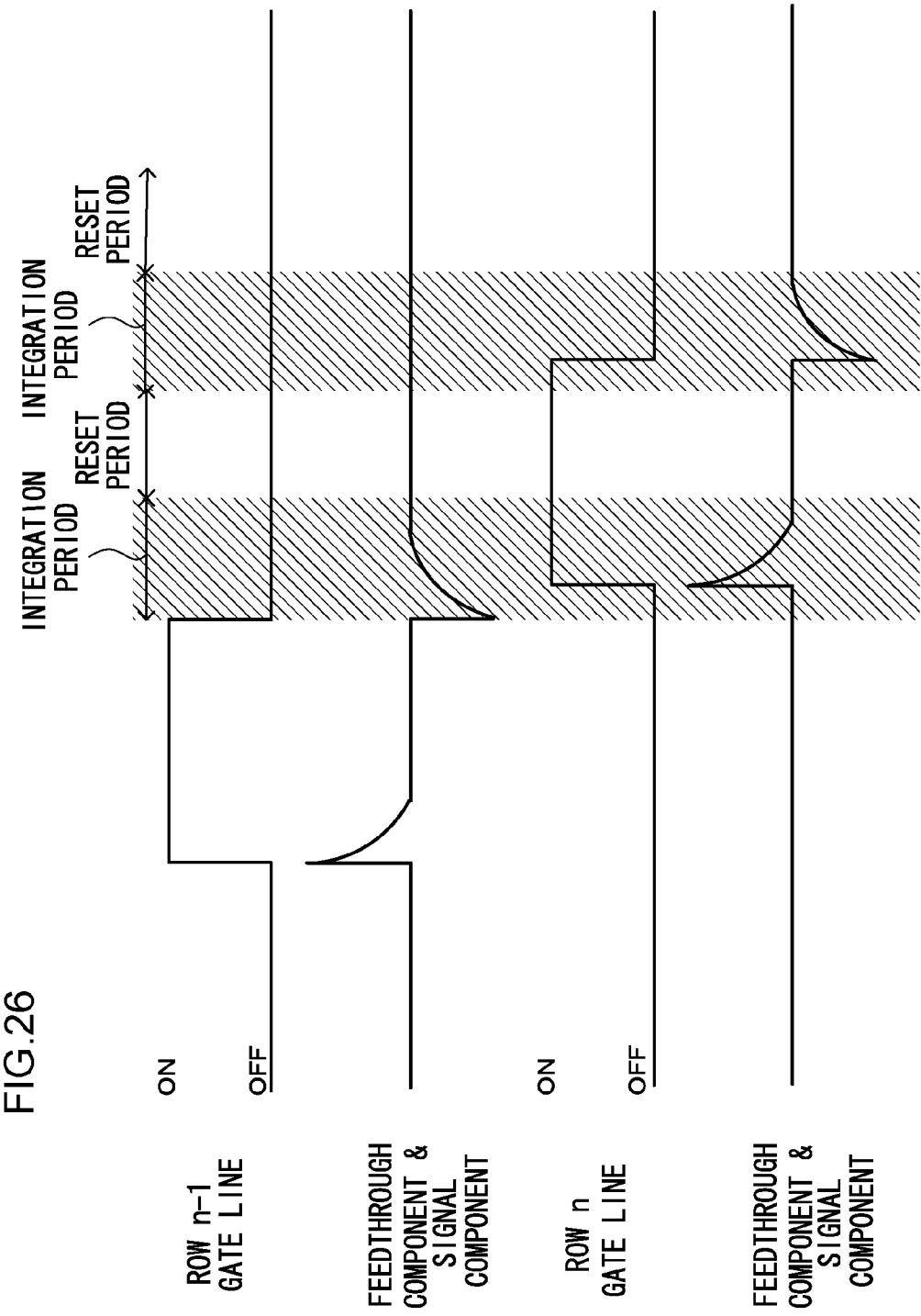
FIG. 26 is a timing chart of another alternative example of the control processing of the electronic cassette in accordance with the second exemplary embodiment.

As a further example, provided the generation period t1 and the generation period t2 are encompassed in the integration period, the timings in the electronic cassette 20 may be controlled such that the TFTs 98 of a subsequent line are turned ON a predetermined duration after TFTs 98 are turned OFF (i.e., the overlap period T is zero), as shown in FIG. 18 and FIG. 26.

The entire periods of the generation period t1 and the generation period t2 need not be encompassed within the integration period. For example, a half-value period of a feedthrough component, a 3σ (σ being the standard deviation) period or the like may be encompassed in the integration period, or a period based on the peak value may be encompassed. Even in a case in which part of a period falls outside the integration period, the feedthrough components encompassed within the integration period may cancel one another out, and therefore the feedthrough components may be suppressed.

In the first exemplary embodiment and second exemplary embodiment described above, the integration period is fixed through a sequence of imaging, but this is not a limitation. The integration period may be altered in accordance with the amplitudes and time constants of the feedthrough components. Moreover, the integration period may be made different for respective regions of the electronic cassette 20.

In the first exemplary embodiment and second exemplary embodiment described above, a temperature is acquired from the temperature detecting section 154 when imaging is beginning, and ON/OFF control of the TFTs 98 is implemented with the same timings for all frames of the imaging, but this is not a limitation. For example, in the electronic cassette 20, the temperature may be acquired from the radiation detector 26, and control applied in accordance with the amplitudes and time constants of the feedthrough components, for each frame or for each cycle of a given number of frames. Moreover, a suitable measurement interval may be altered in accordance with transitions in temperature changes.

The control processing carried out at the electronic cassette 20 is not limited to the control processes described above. For example, these control processes may obviously be used in combinations. As a further example, in the electronic cassette 20, control in accordance with the amplitudes and time constants of the feedthrough components may be applied in a case in which a dose of the radiation X is acquired from an order or acquired from the dose detecting section 155 and the dose is smaller than a predetermined threshold.

It will be clear that, for example, the first exemplary embodiment and the second exemplary embodiment may be used in combination.

It will be clear that, for example, a determination may be made in the electronic cassette 20 as to whether an image is a still image or video image, and control applied in accordance with the amplitudes and time constants of the feedthrough components in the case of a video image. The determination of whether the image is a still image or a video image may be made by acquiring this information from the order, and may be made by comparing a dose acquired from the dose detecting section 155 with a threshold established for video images beforehand or with a dose profile.

In the first exemplary embodiment and second exemplary embodiment described above, as mentioned above, the driving waveforms of the TFTs 98 of the neighboring gate lines 136 are overlapped with one another and the feedthrough components thereof cancel out. However, it will be clear that the same effect can be obtained if driving timings (on state timings) of TFTs 98 that succeed and precede one another are used.

In the first exemplary embodiment and second exemplary embodiment described above, the cassette control section 130 functions so as to implement the control processing described above, but this is not a limitation. For example, the radiation image processing device 14, the console 16 or the like may carry out the control processing described above and output commands to the gate line driver 132 via the cassette control section 130.

In the first exemplary embodiment and second exemplary embodiment described above, TFTs in which the gates turn ON in a case in which positive gate voltages are applied are used as the TFTs 98 that read out the charges from the storage capacitors 96 of the pixels 100, but this is not a limitation (see FIG. 13, FIG. 14, FIG. 17 and FIG. 18 for the first exemplary embodiment and FIG. 21, FIG. 22, FIG. 25 and FIG. 26 for the second exemplary embodiment). For example, TFTs may be used in which the gates are turned ON in a case in which negative gate voltages are applied. The terms "large" and "small" as applied to the gate voltages are intended to mean that the amplitudes of the respective voltages are large and small and that absolute values of the voltages are large and small.

The forms of the pixels 100 are not limited by the first exemplary embodiment and second exemplary embodiment described above. For example, in the first exemplary embodiment and second exemplary embodiment described above, the rectangular pixels 100 are shown in FIG. 4 but the shape of each pixel 100 is not limited to a rectangle and alternative shapes are possible. The arrangement of the pixels 100 is also not limited by the present exemplary embodiments. For example, as a mode in which the pixels 100 are arranged in rows and columns, as shown in FIG. 4, a case in which the pixels 100 are arranged with regularity in a rectangular pattern is illustrated. However, modes are not limited provided the pixels 100 are arranged with regularity in two dimensions.

The arrangement of the gate lines 136 and the signal lines 138 may be put into a mode in which, in contrast to the first exemplary embodiment and second exemplary embodiment described above, the signal lines 138 are arranged in the row direction and the gate lines 136 are arranged in the column direction.

In other respects, configurations, control procedures and the like of the radiation imaging system 10, the electronic cassette 20, the radiation detector 26 and the like described in the above first exemplary embodiment and second exemplary embodiment are examples; it will be clear that these may be modified in accordance with conditions within a scope not departing from the spirit of the present invention.

The radiation X described in the above first exemplary embodiment and second exemplary embodiment is not particularly limited; X-rays, gamma rays and so forth may be employed.

The disclosures of Japanese Patent Application Nos. 2012-053853 and 2012-053854 are incorporated into the present specification by reference in their entirety.

All references, patent applications and technical specifications cited in the present specification are incorporated by reference into the present specification to the same extent as if the individual references, patent applications and technical specifications were specifically and individually recited as being incorporated by reference.

What is claimed is:

1. A radiation imaging device comprising:
   a radiation detector including
      a plurality of scan lines disposed in parallel, and
      a plurality of pixels disposed in a matrix pattern, each pixel including a sensor portion that generates charges in response to irradiated radiation and a switching element that is controlled to ON state or OFF state in accordance with a state of a control signal flowing along a particular scan line, wherein switching elements read out the charges generated by the sensor portions;
   a plurality of amplifier sections, disposed in correspondence with the pixels of the radiation detector, each amplifier section being provided with an integrating capacitor that integrates the charges and a reset section that resets charges in the integrating capacitor, the plurality of amplifier sections amplifying electronic signals based on the charges read out from the corresponding pixels by the switching elements by a predetermined amplification ratio;
   a setting section that sets an integration period of the integrating capacitors, the integration period encompassing
      a first integration period for integrating a feedthrough component generated by a first of the switching elements of a first of the pixels being put into the OFF state by a control signal flowing through a particular scan line, and
      a second integration period for integrating a feedthrough component generated by a second of the switching elements of a second of the pixels, in which a timing for reading out the charges are a plurality of cycles later than the first pixel based on a frame rate, being put into the ON state and the charges read out from the second pixel due to this ON state; and
   a control section is configured to put the first switching element into the OFF state and to put the second switching element into the ON state within the integration period set by the setting section.

2. The radiation imaging device according to claim 1, further comprising a temperature detection section that detects a temperature of the radiation detector,
   wherein a correspondence between temperature and time constants of the feedthrough components is determined in advance, and
   wherein, on the basis of a temperature detected by the temperature detection section, the control section puts the first switching element into the OFF state and puts the second switching element into the ON state at timings in accordance with the time constants of the feedthrough components.

3. The radiation imaging device according to claim 2, wherein the control section puts the first switching element into the OFF state and puts the second switching element into the ON state at timings in accordance with the time constants of the feedthrough components, on the basis of temperatures detected by the temperature detection section at a timing of at least one of a start of imaging or a cycle of a predetermined number of frames.

4. The radiation imaging device according to claim 2, wherein the temperature detection section detects the temperature of at least one predetermined region of a region of the radiation detector on which the radiation is irradiated, and the control section puts the first switching element into the OFF state and puts the second switching element into the ON state at timings in accordance with the time constants of the feedthrough components on the basis of the temperature of the predetermined region detected by the temperature detection section.

5. The radiation imaging device according to claim 2, wherein amplitudes of the feedthrough components are determined in advance for each of predetermined regions of a region of the radiation detector on which the radiation is irradiated, and the control section puts the first switching element into the OFF state and puts the second switching element into the ON state at timings in accordance with the predetermined amplitudes and the time constants of the feedthrough components for each predetermined regions.

6. The radiation imaging device according to claim 5, further comprising a receiving section that receives a designation of the predetermined regions,
   wherein the control section puts the first switching element into the OFF state and puts the second switching element into the ON state at timings in accordance with the predetermined amplitudes and the time constants of the feedthrough components for the predetermined region received by the receiving section.

7. The radiation imaging device according claim 1, wherein the setting section sets the timing for reading out the charges from the second pixel to be a plurality of cycles later than the first pixel, in accordance with a type of video image being imaged with the radiation detector.

8. The radiation imaging device according claim 1 wherein, in a case in which a video image is being imaged with the radiation detector, the control section acquires a frame rate of the video imaging and, in a case in which the frame rate is equal to or higher than a predetermined threshold, puts the first switching element into the OFF state and puts the second switching element into the ON state at timings in accordance with the time constants of the feedthrough components.

9. The radiation imaging device according to claim 1 wherein, in a case in which a dose of the radiation irradiated at the radiation detector is equal to or lower than a predetermined threshold, the control section puts the first switching element into the OFF state and puts the second switching element into the ON state at timings in accordance with the time constants of the feedthrough components.

10. The radiation imaging device according to claim 1 wherein, depending on a type of video imaging, the control section puts the first switching element into the OFF state and puts the second switching element into the ON state at timings in accordance with the time constants of the feedthrough components.

11. The radiation imaging device according to claim 1 wherein, in a case in which a video image is imaged with the radiation detector, the control section acquires a frame rate of the video imaging and, in a case in which the acquired frame rate is equal to or higher than a predetermined threshold, the control section puts the first switching element into the OFF state and puts the second switching element into the ON state at timings such that a period in which the first switching element is in the ON state and a period in which the second switching element is in the ON state overlap, and such that an overlap period of this overlapping is shorter than an overlap period in a case in which the frame rate is lower than the predetermined threshold.

12. The radiation imaging device according to claim 1, wherein the setting section sets to cause the first integration period and the second integration period to overlap.

13. A radiation imaging system comprising:
a radiation irradiation device; and
a radiation imaging device according to claim 1 that detects radiation irradiated from the radiation irradiation device.

14. A control method of a radiation imaging device including a plurality of scan lines disposed in parallel, and a plurality of pixels disposed in a matrix pattern, each pixel including a sensor portion that generates charges in response to irradiated radiation and a switching element that is controlled to ON state or OFF state in accordance with a state of a control signal flowing along a particular scan line, wherein the switching element read out the charges generated by the sensor portions, and a plurality of amplifier sections, disposed in correspondence with the pixels of the radiation detector, each amplifier section being provided with an integrating capacitor that integrates the charges and a reset section that resets charges in the integrating capacitor, the plurality of amplifier sections amplifying electronic signals based on the charges read out from the corresponding pixels by the switching elements by a predetermined amplification ratio, the control method comprising:
setting, by the setting section, an integration period of the integrating capacitors, the integration period encompassing,
a first integration period for integrating a feedthrough component generated by a first of the switching elements of a first of the pixels being put into the OFF state by a control signal flowing through a particular scan line, and
a second integration period for integrating a feedthrough component generated by a second of the switching elements of a second of the pixels, in which a timing for reading out the charges are a plurality of cycles later than the first pixel based on a frame rate, being put into the ON state and the charges read out from the second pixel due to this ON state; and controlling, by a control section, to put the first switching element into the OFF state and to put the second switching element into the ON state within the integration period set by the setting section.

15. A non-transitory computer readable medium storing a control program for a radiation imaging device, the radiation imaging device including a plurality of scan lines disposed in parallel, and a plurality of pixels disposed in a matrix pattern, each pixel including a sensor portion that generates charges in response to irradiated radiation and a switching element that is controlled to ON state or OFF state in accordance with a state of a control signal flowing along a particular scan line, wherein the switching element read out the charges generated by the sensor portions, and a plurality of amplifier sections, disposed in correspondence with the pixels of the radiation detector, each amplifier section being provided with an integrating capacitor that integrates the charges and a reset section that resets charges in the integrating capacitor, and the plurality of amplifier sections amplifying electronic signals based on the charges read out from the corresponding pixels by the switching elements by a predetermined amplification ratio, the control program being executable to cause a computer to function as:
a setting section that sets an integration period of the integrating capacitors, the integration period encompassing
a first integration period for integrating a feedthrough component generated by a first of the switching elements of a first of the pixels being put into the OFF state by a control signal flowing through a particular scan line, and
a second integration period for integrating a feedthrough component generated by a second of the switching elements of a second of the pixels, in which a timing for reading out the charges are a plurality of cycles later than the first pixel based on a frame rate, being put into the ON state and the charges read out from the second pixel due to this ON state; and
a control section that controls to put the first switching element into the OFF state and to put the second switching element into the ON state within the integration period set by the setting section.

* * * * *